US007205459B1

(12) United States Patent  (10) Patent No.: US 7,205,459 B1
Larkins et al.  (45) Date of Patent: Apr. 17, 2007

(54) TRANSFORMABLE INBRED CORN LINE LIZL5 AND METHODS FOR USE THEREOF

(75) Inventors: James R. Larkins, Troy, OH (US); David D. Songstad, Ballwin, MO (US); William L. Petersen, Lodi, WI (US); Hongyi Zhang, St. Charles, MO (US); Michael T. Mann, Groton, CT (US); T. Michael Spencer, Mystic, CT (US); Nancy G. Willetts, Niantic, CT (US)

(73) Assignee: DeKalb Genetics Corporation, DeKalb, IL (US)

( * ) Notice: Subject to any disclaimer, the term of this patent is extended or adjusted under 35 U.S.C. 154(b) by 1336 days.

(21) Appl. No.: 09/606,808

(22) Filed: Jun. 28, 2000

(51) Int. Cl.
  *A01H 5/10* (2006.01)
  *A01H 5/00* (2006.01)
  *A01H 1/00* (2006.01)
  *C12N 5/14* (2006.01)
  *C12N 15/82* (2006.01)
  *C12N 5/04* (2006.01)

(52) U.S. Cl. .................. 800/320.1; 435/412; 435/424; 435/430.1; 435/468; 800/266; 800/274; 800/292; 800/293; 800/294

(58) Field of Classification Search ............ 800/320.1, 800/298, 278, 268, 266, 301, 302, 303; 435/412, 435/424, 430, 430.1
See application file for complete search history.

(56) References Cited

U.S. PATENT DOCUMENTS

| 3,903,645 | A |   | 9/1975  | Bradner ..................... 47/58 |
| 4,368,592 | A |   | 1/1983  | Welch ......................... 47/58 |
| 4,517,763 | A |   | 5/1985  | Beversdorf et al. ........... 47/58 |
| 4,581,847 | A |   | 4/1986  | Hibbard et al. ............... 47/58 |
| 4,594,810 | A |   | 6/1986  | Troyer .......................... 47/58 |
| 4,607,453 | A |   | 8/1986  | Troyer .......................... 47/58 |
| 4,626,610 | A |   | 12/1986 | Sun .............................. 800/1 |
| 4,627,192 | A |   | 12/1986 | Fick ............................. 47/58 |
| 4,629,819 | A |   | 12/1986 | Lindsey ....................... 800/1 |
| 4,642,411 | A |   | 2/1987  | Hibbard et al. ............... 800/1 |
| 4,654,466 | A |   | 3/1987  | Lindsey ....................... 800/1 |
| 4,658,084 | A |   | 4/1987  | Beversdorf et al. ........... 800/1 |
| 4,658,085 | A |   | 4/1987  | Beversdorf et al. ........... 800/1 |
| 4,677,246 | A |   | 6/1987  | Armond et al. ............... 800/1 |
| 4,686,319 | A |   | 8/1987  | Shifriss ........................ 800/1 |
| 4,731,499 | A |   | 3/1988  | Puskaric et al. .............. 800/1 |
| 4,737,596 | A |   | 4/1988  | Seifert et al. ................. 800/1 |
| 4,751,347 | A |   | 6/1988  | Erickson ...................... 800/1 |
| 4,767,888 | A |   | 8/1988  | Ayotte et al. ................. 800/1 |
| 5,276,263 | A |   | 1/1994  | Foley ........................ 800/200 |
| 5,523,520 | A | * | 6/1996  | Hunsperger et al. ..... 800/323.1 |
| 5,936,145 | A | * | 8/1999  | Bradbury |

FOREIGN PATENT DOCUMENTS

EP   0 270 356   2/1987

OTHER PUBLICATIONS

Kraft et al., Theor. Appl. Genet., 2000, vol. 101, pp. 323-326.*
Eshed et al., Genetics, 1996, vol. 143, pp. 1807-1817.*
Chandler et al., "Two Regulatory Genes of the Maize Anthocyanin Pathway Are Homologous: Isolation of B Utilizing R Genomic Sequences," *The Plant Cell*, 1:1175-1183, 1989.
Culotta, "How many Genes Had to Change to Produce Corn," *Science*, 252:1792-1793, 1991.
Duvick, "Genetic Contributions to Yield Gains of U.S. Hybrid Maize, 1930 to 1980," *Genetic Contributions to Yield Gains of Five Major Crop Plants*: Proceedings of a Symposium sponsored by Div. C-1, Crop Science Society of America, Dec. 2, 1981 in Atlanta, Georgia; W.R. Fehr, Crop Science Society of America and American Society of Agronomy, Madison, Wisconsin, pp. 15-47.
Green & Rhodes, "Plant Regeneration in Tissue Cultures of Maize," *Maize for Biological Research*, ed. W.F. Sheridan, A Special Publication of the Plant Molecular Biology Association, pp. 367-372, 1982.
Hauptmann et al., "Evaluation of Selectable Markers for Obtaining Stable Transformants in the *Gramineae*," *Plant Physiol.*, 86:602-606, 1988.
Larson & Hanway, "Corn Production," *Corn and Corn Improvement*, ed. G.F. Sprague, No. 18 in Agronomy Series, American Society of Agronomy, Inc., Madison, Wisconsin, pp. 625-669, 1977.
Ludwig et al., "A Regulatory Gene as a Novel Visible Marker for Maize Transformation," *Science*, 247:449-450, 1990.
Poehlman, *Breeding Field Crops*, 3rd ed., AVI Publishing Company, Westport, Connecticut, pp. 469-481, 1987.
Sprague & Eberhart, "Corn Breeding," *Corn and Corn Improvements*, ed. G.F. Sprague, No. 18 in Agronomy Series, American Society of Agronomy, Inc., Madison, Wisconsin, pp. 305-323, 1977.
Troyer, "A Retrospective View of Corn Genetic Resources," *Journal of Heredity*, 81:17-24, 1990.
Withers & King, "Proline: A Novel Cryoprotectant for the Freeze Preservation of Cultured Cells of *Zea mays* L.," *Plant Physiol.*, 64:675-578, 1979.

(Continued)

*Primary Examiner*—Ashwin Mehta
(74) *Attorney, Agent, or Firm*—Fulbright & Jaworski L.L.P.

(57) ABSTRACT

According to the invention, there is provided an inbred corn plant designated LIZL5. This invention thus relates to the plants, seeds and tissue cultures of the inbred corn plant LIZL5, and to methods for producing a corn plant produced by crossing the inbred corn plant LIZL5 with itself or with another corn plant, such as another inbred. This invention further relates to corn seeds and plants produced by crossing the inbred plant LIZL5 with another corn plant, such as another inbred, and to crosses with related species. This invention further relates to the inbred and hybrid genetic complements of the inbred corn plant LIZL5, and also to the SSR and genetic isozyme typing profiles of inbred corn plant LIZL5. This invention further relates to methods of transforming the inbred LIZL5 and cells thereof, transformed plants produced by these methods, progeny transgenic plants, and seed derived therefrom.

38 Claims, 2 Drawing Sheets

OTHER PUBLICATIONS

Armstrong & Green, "Establishment and Maintenance of Friable Embryogenic *Maize callus* and the Involvement of L-Proline," *Planta*, 164:207-214, 1985.

Edallo et al., "Chromosomal Variation and Frequency of Spontaneous Mutation Associated with *in vitro* Culture and Plant Regeneration in Maize," *Maydica*, 26:39-56, 1981.

Gordon-Kamm et al., "Transformation of Maize Cells and Regeneration of Fertile Transgenic Plants," *The Plant Cell*, 2:603-618, 1990.

Green & Phillips, "Plant Regeneration from Tissue Cultures of Maize," *Crop Science*, 15:417-421, 1975.

Hallauer et al., "Corn Breeding," *Corn and Corn Improvement*, eds., Sprague et al., Madison, Wisconsin, Ch. 8, pp. 463-564, 1988.

*MBS, Inc., Genetics Handbook*, 17th ed., MBS, Inc., Ames, Iowa, pp. 3 & 19, 1990.

Meghji et al., "Inbreeding Depression, Inbred and Hybrid Grain Yields, and Other traits of Maize Genotypes Representing Three Eras," *Crop Science*, 24:545-549, 1984.

Phillips et al., "Cell/Tissue Culture and *in vitro* Manipulation," *Corn and Corn Improvement*, eds., Sprague et al., Ch. 5, pp. 345-387, 1988.

Rieger et al., *Glossary of Genetics and Cytogenetics, Classical and Molecular*, Springer-Verlag, Berlin, p. 116, 1976.

Rhodes et al., Genetically Transformed Maize Plants from Protoplasts, *Science*, 240:204-207, 1988.

Wright, "Commercial Hybrid Seed," *Hybridization of Crop Plants*, Fehr et al., eds. Am. Soc. of agron.-Crop Sci. Soc. of Am., Madison, Wisconsin, Ch. 8, pp. 161-176, 1980.

Wych, "Production of Hybrid Seed Corn," *Corn and Corn Improvement*, eds., Sprague et al., Madison, Wisconsin, Ch. 9, pp. 565-607, 1988.

Gerdes and Tracy, "Diverstiy of Historically Important Sweet Corn Inbredsas Estimated by RFLP's, Morphology, Isozymes, and Pedigree," *Crop Science*, 34(1):26-33, 1994.

Conger et al., "Somatic Embryogenesis from Cultured Leaf Segments of *Zea mays,*" *Plant Cell Reports*, 6:345-347, 1987.

Duncan et al., "The Production of Callus Capable of Plant Regeneration from Immature Embryos of Numerous *Zea mays* Genotypes," *Planta*, 165:322-332, 1985.

Fehr (ed.), *Principles of Cultivar Development*, vol. 1: *Theory and Technique*, pp. 360-376, 1987.

Gaillard et al., "Optimization of Maize Microspore Isolation and Culture Condition for Reliable Plant Regeneration," *Plant Cell Reports*, 10(2):55, 1991.

Jensen, "Chromosome Doubling Techniques in Haploids," *Haploids and Higher Plants—Advances and Potentials, Proceedings of the First International Symposium*, University of Guelph, Jun. 10-14, 1974.

Nienhuis et al., "Restriction Fragment Length Polymorphism Analysis of Loci Associated with Insect Resistance in Tomato," *Crop Science*, 27:797-803, 1987.

Pace et al., "Anther Culture of Maize and the Visualization of Embryogenic Microspores by Fluorescent Microscopy," *Theoretical and Applied Genetics*, 73:863-869, 1987.

Poehlman & Sleper (eds), *Breeding Field Crops*, 4th Ed., pp. 172-175, 1995.

Rao et al., "Somatic Embryogenesis in *Glume callus* Cultures," *Maize Genetics Cooperation Newsletter*, vol. 60, 1986.

Songstad et al. "Effect of 1-Aminocyclopropate-1-Carboxylic Acid, Silver Nitrate, and Norbornadiene on Plant Regeneration from *Maize callus* Cultures," *Plant Cell Reports*, 7:262-265, 1988.

Stuber et al., "Techniques and scoring procedures for starch gel electrophoresis of enzymes of *Maize c. Zea mays*, L.," *Tech. Bull.*, N. Carolina Agric. Res. Serv., vol. 286, 1988.

Wan et al., "Efficient Production of Doubled Haploid Plants Through Colchicine Treatment of Anther-Derived *Maize callus*," *Theoretical and Applied Genetics*, 77:889-892, 1989.

Beckmann and Soller, "Restriction Fragment Length Polymorphisms in Plant Genetic Improvement," Oxfors Surveys of Plant Molecular & Cell Biology, 3:196-250, 1986.

Smith and Smith, "Restriction Fragment Length Polymorphisms Can Differentiate Among U.S. Maize Hybrids," Crop Sci., 31:893-899, 1991.

U.S. Appl. No. 08/181,019, entitled "Inbred Corn Plant MM402A", filed Jan. 13, 1994, B. Woodruff.

U.S. Appl. No. 08/702,920, entitled "Inbred Corn Plant NL054B and Seeds Thereof", filed Aug. 26, 1996, G. Stangland.

* cited by examiner

TRANSFORMABLE INBRED CORN LINE LIZL5 AND METHODS FOR USE THEREOF

BACKGROUND OF THE INVENTION

1. Field of the Invention

The present invention relates generally to the field of corn breeding. In particular, the invention relates to inbred corn seed and plants designated LIZL5, and derivatives, tissue cultures thereof, methods of transformation of plants or parts thereof of the plant designated LIZL5 and transformants derived thereof

2. Description of Related Art

The goal of field crop breeding is to combine various desirable traits in a single variety/hybrid. Such desirable traits include greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size.

Breeding techniques take advantage of a plant's method of pollination. There are two general methods of pollination: a plant self-pollinates if pollen from one flower is transferred to the same or another flower of the same plant. A plant cross-pollinates if pollen comes to it from a flower on a different plant.

Corn plants (*Zea mays* L.) can be bred by both self-pollination and cross-pollination. Both types of pollination involve the corn plant's flowers. Corn has separate male and female flowers on the same plant, located on the tassel and the ear, respectively. Natural pollination occurs in corn when wind blows pollen from the tassels to the silks that protrude from the tops of the ear shoot.

Plants that have been self-pollinated and selected for type over many generations become homozygous at almost all gene loci and produce a uniform population of true breeding progeny, a homozygous plant. A cross between two such homozygous plants produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform corn plant hybrids requires the development of homozygous inbred plants, the crossing of these inbred plants, and the evaluation of the crosses. Pedigree breeding and recurrent selection are examples of breeding methods used to develop inbred plants from breeding populations. Those breeding methods combine the genetic backgrounds from two or more inbred plants or various other broad-based sources into breeding pools from which new inbred plants are developed by selfing and selection of desired phenotypes. The new inbreds are crossed with other inbred plants and the hybrids from these crosses are evaluated to determine which of those have commercial potential.

The pedigree breeding method involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and selected in successive generations. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. After at least five generations, the inbred plant is considered genetically pure.

Backcrossing can also be used to improve an inbred plant. Backcrossing transfers a specific desirable trait from one inbred or non-inbred source to an inbred that lacks that trait. Methods of genetic transformation have allowed the breeder to exploit an increased variety of specific traits, some of which, such as insect resistance mediated by endotoxins from *Bacillus thuringiensis* or resistance to glyphosate mediated by a non-plant derived glyphosate resistant EPSPS enzyme such as the *Agrobacterium* CP4 enzyme, are only available to the breeder, because they can be introduced into the plant through transformation methods. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

A single cross hybrid corn variety is the cross of two inbred plants, each of which has a genotype which complements the genotype of the other. The hybrid progeny of the first generation is designated $F_1$. Typically, $F_1$ hybrids are more vigorous than their inbred parents. This hybrid vigor, or heterosis, is manifested in many polygenic traits, including markedly improved yields, better stalks, better roots, better uniformity and better insect and disease resistance. In the development of hybrids only the $F_1$ hybrid plants are typically sought. An $F_1$ single cross hybrid is produced when two inbred plants are crossed. A double cross hybrid is produced from four inbred plants crossed in pairs (A×B and C×D) and then the two $F_1$ hybrids are crossed again (A×B)×(C×D).

The development of a hybrid corn variety involves three steps: (1) the selection of plants from various germplasm pools; (2) the selfing of the selected plants for several generations to produce a series of inbred plants, which, although different from each other, each breed true and are highly uniform; and (3) crossing the selected inbred plants with unrelated inbred plants to produce the hybrid progeny ($F_1$). During the inbreeding process in corn, the vigor of the plants decreases. Vigor is restored when two unrelated inbred plants are crossed to produce the hybrid progeny ($F_1$). An important consequence of the homozygosity and homogeneity of the inbred plants is that the hybrid between any two inbreds is always the same. Once the inbreds that give a superior hybrid have been identified, hybrid seed can be reproduced indefinitely as long as the homogeneity of the inbred parents is maintained. Conversely, much of the hybrid vigor exhibited by $F_1$ hybrids is lost in the next generation ($F_2$). Consequently, seed from hybrid varieties is not used for planting stock. It is not generally beneficial for farmers to save seed of $F_1$ hybrids. Rather, farmers purchase $F_1$ hybrid seed for planting every year.

North American farmers plant tens of millions of acres of corn at the present time and there are extensive national and international commercial corn breeding programs. A continuing goal of these corn breeding programs is to develop corn hybrids that are based on stable inbred plants and have one or more desirable characteristics. To accomplish this goal, the corn breeder must select and develop superior inbred parental plants.

SUMMARY OF THE INVENTION

In one aspect, the present invention provides a corn plant designated LIZL5. Also provided are corn plants having all the physiological and morphological characteristics of corn plant LIZL5. The inbred corn plant of the invention may further comprise, or have, a cytoplasmic or nuclear factor that is capable of conferring male sterility. Parts of the corn plant of the present invention are also provided, for example, pollen obtained from an inbred plant and an ovule of the inbred plant.

The invention also concerns seed of the corn plant LIZL5. A sample of this seed has been deposited under ATCC Accession No. PTA-2192. The inbred corn seed of the invention may be provided as an essentially homogeneous population of inbred corn seed of the corn plant designated LIZL5. Essentially homogeneous populations of inbred seed are those that consist essentially of the particular inbred seed, and are generally free from substantial numbers of other seed, so that the inbred seed forms between about 90% and about 100% of the total seed, and preferably, between about 95% and about 100% of the total seed. Most preferably, an essentially homogeneous population of inbred corn seed will contain between about 98.5%, 99%, 99.5% and about 99.9% of inbred seed, as measured by seed grow outs.

Therefore, in the practice of the present invention, inbred seed generally forms at least about 97% of the total seed. However, even if a population of inbred corn seed was found, for some reason, to contain about 50%, or even about 20% or 15% of inbred seed, this would still be distinguished from the small fraction of inbred seed that may be found within a population of hybrid seed, e.g., within a bag of hybrid seed. In such a bag of hybrid seed offered for sale, the Governmental regulations require that the hybrid seed be at least about 95% of the total seed. In the most preferred practice of the invention, the female inbred seed that may be found within a bag of hybrid seed will be about 1% of the total seed, or less, and the male inbred seed that may be found within a bag of hybrid seed will be negligible, i.e., will be on the order of about a maximum of 1 per 100,000, and usually less than this value.

The population of inbred corn seed of the invention can further be particularly defined as being essentially free from hybrid seed. The inbred seed population may be separately grown to provide an essentially homogeneous population of inbred corn plants designated LIZL5.

In another aspect of the invention, single locus converted plants of LIZL5 are provided. The single transferred locus may preferably be a dominant or recessive allele. Preferably, the single transferred locus will confer such traits as male sterility, yield stability, waxy starch, yield enhancement, industrial usage, herbicide resistance, insect resistance, resistance to bacterial, fungal, nematode or viral disease, male fertility, and enhanced nutritional quality. The single locus may be a naturally occurring maize gene or a transgene introduced through genetic transformation techniques. When introduced through transformation, a single locus may comprise one or more transgenes integrated at a single chromosomal location.

In yet another aspect of the invention, an inbred corn plant designated LIZL5 is provided, wherein a cytoplasmically-inherited trait has been introduced into said inbred plant. Such cytoplasmically-inherited traits are passed to progeny through the female parent in a particular cross. An exemplary cytoplasmically-inherited trait is the male sterility trait. A cytoplasmically inherited trait may be a naturally occurring maize trait or a trait introduced through genetic transformation techniques.

In another aspect of the invention, a tissue culture of regenerable cells of inbred corn plant LIZL5 is provided. The tissue culture will preferably be capable of regenerating plants capable of expressing all of the physiological and morphological characteristics of the foregoing inbred corn plant, and of regenerating plants having substantially the same genotype as the foregoing inbred corn plant. Examples of some of the physiological and morphological characteristics of the inbred corn plant LIZL5 include characteristics related to yield, maturity, and kernel quality, each of which are specifically disclosed herein. The regenerable cells in such tissue cultures will preferably be derived from embryos, meristematic cells, immature tassels, microspores, pollen, leaves, anthers, roots, root tips, silk, flowers, kernels, ears, cobs, husks, or stalks, or callus or protoplasts derived from these tissues. Still further, the present invention provides corn plants regenerated from the tissue cultures of the invention, the plants having all the physiological and morphological characteristics of corn plant LIZL5.

In yet another aspect of the invention, processes are provided for producing corn seeds or plants, which processes generally comprise crossing a first parent corn plant with a second parent corn plant, wherein at least one of the first or second parent corn plants is the inbred corn plant designated LIZL5. These processes may be further exemplified as processes for preparing hybrid corn seed or plants, wherein a first inbred corn plant is crossed with a second, distinct inbred corn plant to provide a hybrid that has, as one of its parents, the inbred corn plant LIZL5. In these processes, the step of crossing will result in the production of seed. The seed production occurs regardless of whether the seed is collected or not.

In a preferred embodiment of the invention, crossing comprises planting in pollinating proximity seeds of a first and second parent corn plant, and preferably, seeds of a first inbred corn plant and a second, distinct inbred corn plant; cultivating or growing the seeds of said first and second parent corn plants into plants that bear flowers; emasculating the male flowers of the first or second parent corn plant, (i.e., treating or manipulating the flowers so as to prevent pollen production, in order to produce an emasculated parent corn plant) allowing natural cross-pollination to occur between the first and second parent corn plants; and harvesting the seeds from the emasculated parent corn plant. Where desired, the harvested seed is grown to produce a corn plant or hybrid corn plant.

The present invention also provides corn seed and plants produced by a process that comprises crossing a first parent corn plant with a second parent corn plant, wherein at least one of the first or second parent corn plants is the inbred corn plant designated LIZL5. In one embodiment of the invention, corn plants produced by the process are first generation ($F_1$) hybrid corn plants produced by crossing an inbred in accordance with the invention with another, distinct inbred. The present invention further contemplates seed of an $F_1$ hybrid corn plant. Therefore, certain exemplary embodiments of the invention provide an $F_1$ hybrid corn plant and seed thereof. An example of such a hybrid which can be produced with the inbred designated LIZL5 is the hybrid corn plant designated 7026255.

In still yet another aspect of the invention, an inbred genetic complement of the corn plant designated LIZL5 is provided. The phrase "genetic complement" is used to refer to the aggregate of nucleotide sequences, the expression of which sequences defines the phenotype of, in the present case, a corn plant, or a cell or tissue of that plant. An inbred genetic complement thus represents the genetic make up of an inbred cell, tissue or plant, and a hybrid genetic complement represents the genetic make up of a hybrid cell, tissue or plant. The invention thus provides corn plant cells that have a genetic complement in accordance with the inbred corn plant cells disclosed herein, and plants, seeds and diploid plants containing such cells.

Plant genetic complements may be assessed by genetic marker profiles, and by the expression of phenotypic traits that are characteristic of the expression of the genetic complement, e.g., isozyme typing profiles. Thus, such corn plant cells may be defined as having an SSR genetic marker profile in accordance with the profile shown in Table 6, or a genetic isozyme typing profile in accordance with the profile shown in Table 7, or having both an SSR genetic marker profile and a genetic isozyme typing profile in accordance with the profiles shown in Table 6 and Table 7. It is understood that LIZL5 could also be identified by other types of genetic markers such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by corn plant cells, tissues, plants, and seeds, formed by the combination of a haploid genetic complement of an inbred corn plant of the invention with a haploid genetic complement of a second corn plant, preferably, another, distinct inbred corn plant. In another aspect, the present invention provides a corn plant regenerated from a tissue culture that comprises a hybrid genetic complement of this invention.

In still yet another aspect, the invention provides a method of preparing a transgenic maize cell comprising: a) providing cells of inbred corn plant LIZL5, b) contacting the cells with a pre-selected DNA; and c) identifying at least a first transgenic cell of inbred corn plant LIZL5 which has been transformed with the pre-selected DNA. In certain embodiments of the invention, the method may further comprise the step of: d) regenerating a fertile transgenic plant from the transgenic cell. In the method, the transforming may be carried out by any method, including, for example, microprojectile bombardment, PEG mediated transformation of protoplasts, electroporation, silicon carbide fiber mediated transformation, or Agrobacterium-mediated transformation.

In still yet another aspect, the invention provides a fertile transgenic maize plant prepared from a transformed LIZL5 cell, or a progeny plant of any generation of such a plant. Such a plant may be prepared by a method of the invention or any other method. Also provided by the invention is a seed of such fertile transgenic maize plants, wherein the seed comprises said pre-selected DNA. Still further provided by the invention is a plant grown from such seed, said plant comprising the pre-selected DNA.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

I. Definitions of Plant Characteristics

Figure 1:
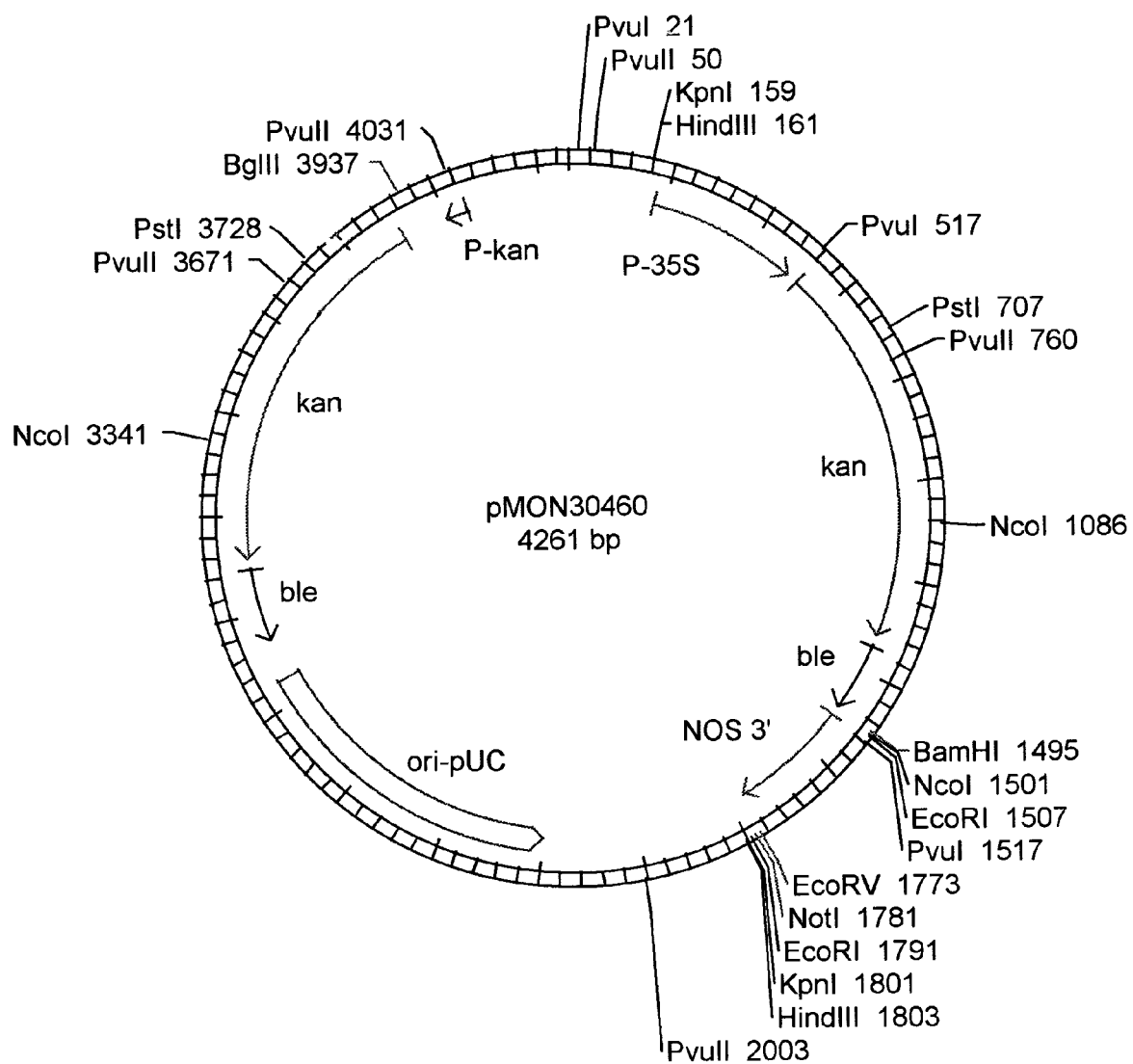
FIG. 1 is a depiction of plasmid vector pMON30460. The plasmid comprises a Cauliflower Mosaic Virus 35S promoter operably linked to a neomycin phosphotransferase II sequence with termination and polyadenylation signal sequences derived from the nopaline synthase gene.

Barren Plants: Plants that are barren, i.e., lack an ear with grain, or have an ear with only a few scattered kernels.

Cg: *Colletotrichum graminicola* rating. Rating times 10 is approximately equal to percent total plant infection.

CLN: Corn Lethal Necrosis (combination of Maize Chlorotic Mottle Virus and Maize Dwarf Mosaic virus) rating: numerical ratings are based on a severity scale where 1=most resistant to 9=susceptible.

Cn: *Corynebacterium nebraskense* rating. Rating times 10 is approximately equal to percent total plant infection.

Cz: *Cercospora zeae-maydis* rating. Rating times 10 is approximately equal to percent total plant infection.

Dgg: *Diatraea grandiosella* girdling rating (values are percent plants girdled and stalk lodged).

Dropped Ears: Ears that have fallen from the plant to the ground.

Dsp: *Diabrotica* species root ratings (1=least affected to 9=severe pruning).

Ear-Attitude: The attitude or position of the ear at harvest scored as upright, horizontal, or pendant.

Ear-Cob Color: The color of the cob, scored as white, pink, red, or brown.

Ear-Cob Diameter: The average diameter of the cob measured at the midpoint.

Ear-Cob Strength: A measure of mechanical strength of the cobs to breakage, scored as strong or weak.

Ear-Diameter: The average diameter of the ear at its midpoint.

Ear-Dry Husk Color: The color of the husks at harvest scored as buff, red, or purple.

Ear-Fresh Husk Color: The color of the husks 1 to 2 weeks after pollination scored as green, red, or purple.

Ear-Husk Bract: The length of an average husk leaf scored as short, medium, or long.

Ear-Husk Cover: The average distance from the tip of the ear to the tip of the husks. Minimum value no less than zero.

Ear-Husk Opening: An evaluation of husk tightness at harvest scored as tight, intermediate, or open.

Ear-Length: The average length of the ear.

Ear-Number Per Stalk: The average number of ears per plant.

Ear-Shank Internodes: The average number of internodes on the ear shank.

Ear-Shank Length: The average length of the ear shank.

Ear-Shelling Percent: The average of the shelled grain weight divided by the sum of the shelled grain weight and cob weight for a single ear.

Ear-Silk Color: The color of the silk observed 2 to 3 days after silk emergence scored as green-yellow, yellow, pink, red, or purple.

Ear-Taper (Shape): The taper or shape of the ear scored as conical, semi-conical, or cylindrical.

Ear-Weight: The average weight of an ear.

Early Stand: The percent of plants that emerge from the ground as determined in the early spring.

ER: Ear rot rating (values approximate percent ear rotted).

Final Stand Count: The number of plants just prior to harvest.

GDUs: Growing degree units which are calculated by the Barger Method, where the heat units for a 24-h period are calculated as GDUs=[(Maximum daily temperature+Minimum daily temperature)/2]−50. The highest maximum daily temperature used is 86° F. and the lowest minimum temperature used is 50° F.

GDUs to Shed: The number of growing degree units (GDUs) or heat units required for an inbred line or hybrid to have approximately 50% of the plants shedding pollen as measured from time of planting. GDUs to shed is determined by summing the individual GDU daily values from planting date to the date of 50% pollen shed.

GDUs to Silk: The number of growing degree units for an inbred line or hybrid to have approximately 50% of the plants with silk emergence as measured from time of planting. GDUs to silk is determined by summing the individual GDU daily values from planting date to the date of 50% silking.

Hc2: *Helminthosporium carbonum* race 2 rating. Rating times 10 is approximately equal to percent total plant infection.

Hc3: *Helminthosporium carbonum* race 3 rating. Rating times 10 is approximately equal to percent total plant infection.

Hm: *Helminthosporium maydis* race 0 rating. Rating times 10 is approximately equal to percent total plant infection.

Ht1: *Helminthosporium turcicum* race 1 rating. Rating times 10 is approximately equal to percent total plant infection.

Ht2: *Helminthosporium turcicum* race 2 rating. Rating times 10 is approximately equal to percent total plant infection.

HtG: Chlorotic-lesion type resistance. +=indicates the presence of Ht chlorotic-lesion type resistance; −=indicates absence of Ht chlorotic-lesion type resistance; and +/−=indicates segregation of Ht chlorotic-lesion type resistance. Rating times 10 is approximately equal to percent total plant infection.

Kernel-Aleurone Color: The color of the aleurone scored as white, pink, tan, brown, bronze, red, purple, pale purple, colorless, or variegated.

Kernel-Cap Color: The color of the kernel cap observed at dry stage, scored as white, lemon-yellow, yellow, or orange.

Kernel-Endosperm Color: The color of the endosperm scored as white, pale yellow, or yellow.

Kernel-Endosperm Type: The type of endosperm scored as normal, waxy, or opaque.

Kernel-Grade: The percent of kernels that are classified as rounds.

Kernel-Length: The average distance from the cap of the kernel to the pedicel.

Kernel-Number Per Row: The average number of kernels in a single row.

Kernel-Pericarp Color: The color of the pericarp scored as colorless, red-white crown, tan, bronze, brown, light red, cherry red, or variegated.

Kernel-Row Direction: The direction of the kernel rows on the ear scored as straight, slightly curved, spiral, or indistinct (scattered).

Kernel-Row Number: The average number of rows of kernels on a single ear.

Kernel-Side Color: The color of the kernel side observed at the dry stage, scored as white, pale yellow, yellow, orange, red, or brown.

Kernel-Thickness: The distance across the narrow side of the kernel.

Kernel-Type: The type of kernel scored as dent, flint, or intermediate.

Kernel-Weight: The average weight of a predetermined number of kernels.

Kernel-Width: The distance across the flat side of the kernel.

Kz: *Kabatiella zeae* rating. Rating times 10 is approximately equal to percent total plant infection.

Leaf-Angle: Angle of the upper leaves to the stalk scored as upright (0 to 30 degrees), intermediate (30 to 60 degrees), or lax (60 to 90 degrees).

Leaf-Color: The color of the leaves 1 to 2 weeks after pollination scored as light green, medium green, dark green, or very dark green.

Leaf-Length: The average length of the primary ear leaf.

Leaf-Longitudinal Creases: A rating of the number of longitudinal creases on the leaf surface 1 to 2 weeks after pollination. Creases are scored as absent, few, or many.

Leaf-Marginal Waves: A rating of the waviness of the leaf margin 1 to 2 weeks after pollination. Rated as none, few, or many.

Leaf-Number: The average number of leaves of a mature plant. Counting begins with the cotyledonary leaf and ends with the flag leaf.

Leaf-Sheath Anthocyanin: A rating of the level of anthocyanin in the leaf sheath 1 to 2 weeks after pollination, scored as absent, basal-weak, basal-strong, weak or strong.

Leaf-Sheath Pubescence: A rating of the pubescence of the leaf sheath. Ratings are taken 1 to 2 weeks after pollination and scored as light, medium, or heavy.

Leaf-Width: The average width of the primary ear leaf measured at its widest point.

LSS: Late season standability (values times 10 approximate percent plants lodged in disease evaluation plots).

Moisture: The moisture of the grain at harvest.

On1: *Ostrinia nubilalis* 1st brood rating (1=resistant to 9=susceptible).

On2: *Ostrinia nubilalis* 2nd brood rating (1=resistant to 9=susceptible).

Relative Maturity: A maturity rating based on regression analysis. The regression analysis is developed by utilizing check hybrids and their previously established day rating versus actual harvest moistures. Harvest moisture on the hybrid in question is determined and that moisture value is inserted into the regression equation to yield a relative maturity.

Root Lodging: Root lodging is the percentage of plants that root lodge. A plant is counted as root lodged if a portion of the plant leans from the vertical axis by approximately 30 degrees or more.

Seedling Color: Color of leaves at the 6 to 8 leaf stage.

Seedling Height: Plant height at the 6 to 8 leaf stage.

Seedling Vigor: A visual rating of the amount of vegetative growth on a 1 to 9 scale, where 1 equals best. The score is taken when the average entry in a trial is at the fifth leaf stage.

Selection Index: The selection index gives a single measure of hybrid's worth based on information from multiple traits. One of the traits that is almost always included is yield. Traits may be weighted according to the level of importance assigned to them.

Sr: *Sphacelotheca reiliana* rating is actual percent infection.

Stalk-Anthocyanin: A rating of the amount of anthocyanin pigmentation in the stalk. The stalk is rated 1 to 2 weeks after pollination as absent, basal-weak, basal-strong, weak, or strong.

Stalk-Brace Root Color: The color of the brace roots observed 1 to 2 weeks after pollination as green, red, or purple.

Stalk-Diameter: The average diameter of the lowest visible internode of the stalk.

Stalk-Ear Height: The average height of the ear measured from the ground to the point of attachment of the ear shank of the top developed ear to the stalk.

Stalk-Internode Direction: The direction of the stalk internode observed after pollination as straight or zigzag.

Stalk-Internode Length: The average length of the internode above the primary ear.

Stalk Lodging: The percentage of plants that did stalk lodge. Plants are counted as stalk lodged if the plant is broken over or off below the ear.

Stalk-Nodes With Brace Roots: The average number of nodes having brace roots per plant.

Stalk-Plant Height: The average height of the plant as measured from the soil to the tip of the tassel.

Stalk-Tillers: The percent of plants that have tillers. A tiller is defined as a secondary shoot that has developed as a tassel capable of shedding pollen.

Staygreen: Staygreen is a measure of general plant health near the time of black layer formation (physiological maturity). It is usually recorded at the time the ear husks of most entries within a trial have turned a mature color. Scoring is on a 1 to 9 basis where 1 equals best.

STR: Stalk rot rating (values represent severity rating of 1=25% of inoculated internode rotted to 9=entire stalk rotted and collapsed).

SVC: Southeastern Virus Complex (combination of Maize Chlorotic Dwarf Virus and Maize Dwarf Mosaic Virus) rating; numerical ratings are based on a severity scale where 1=most resistant to 9=susceptible (1988 reactions are largely Maize Dwarf Mosaic Virus reactions).

Tassel-Anther Color: The color of the anthers at 50% pollen shed scored as green-yellow, yellow, pink, red, or purple.

Tassel-Attitude: The attitude of the tassel after pollination scored as open or compact.

Tassel-Branch Angle: The angle of an average tassel branch to the main stem of the tassel scored as upright (less than 30 degrees), intermediate (30 to 45 degrees), or lax (greater than 45 degrees).

Tassel-Branch Number: The average number of primary tassel branches.

Tassel-Glume Band: The closed anthocyanin band at the base of the glume scored as present or absent.

Tassel-Glume Color: The color of the glumes at 50% shed scored as green, red, or purple.

Tassel-Length: The length of the tassel measured from the base of the bottom tassel branch to the tassel tip.

Tassel-Peduncle Length: The average length of the tassel peduncle, measured from the base of the flag leaf to the base of the bottom tassel branch.

Tassel-Pollen Shed: A visual rating of pollen shed determined by tapping the tassel and observing the pollen flow of approximately five plants per entry. Rated on a 1 to 9 scale where 9=sterile, 1=most pollen.

Tassel-Spike Length: The length of the spike measured from the base of the top tassel branch to the tassel tip.

Test Weight: Weight of the grain in pounds for a given volume (bushel) adjusted to 15.5% moisture.

Yield: Yield of grain at harvest adjusted to 15.5% moisture.

II. Other Definitions

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny back to one of the parents, for example, a first generation hybrid ($F_1$) with one of the parental genotypes of the $F_1$ hybrid.

Chromatography: A technique wherein a mixture of dissolved substances are bound to a solid support followed by passing a column of fluid across the solid support and varying the composition of the fluid. The components of the mixture are separated by selective elution.

Crossing: The pollination of a female flower of a corn plant, thereby resulting in the production of seed from the flower.

Cross-pollination: Fertilization by the union of two gametes from different plants.

Diploid: A cell or organism having two sets of chromosomes.

Electrophoresis: A process by which particles suspended in a fluid or a gel matrix are moved under the action of an electrical field, and thereby separated according to their charge and molecular weight. This method of separation is well known to those skilled in the art and is typically applied to separating various forms of enzymes and of DNA fragments produced by restriction endonucleases.

Emasculate: The removal of plant male sex organs or the inactivation of the organs with a chemical agent or a cytoplasmic or nuclear genetic factor conferring male sterility.

Enzymes: Molecules which can act as catalysts in biological reactions.

$F_1$ Hybrid: The first generation progeny of the cross of two plants.

Genetic Complement: An aggregate of nucleotide sequences, the expression of which sequences defines the phenotype in corn plants, or components of plants including cells or tissue.

Genotype: The genetic constitution of a cell or organism.

Haploid: A cell or organism having one set of the two sets of chromosomes in a diploid.

Isozymes: Detectable variants of an enzyme, the variants catalyzing the same reaction(s) but differing from each other, e.g., in primary structure and/or electrophoretic mobility. The differences between isozymes are under single gene, codominant control. Consequently, electrophoretic separation to produce band patterns can be equated to different alleles at the DNA level. Structural differences that do not alter charge cannot be detected by this method.

Isozyme typing profile: A profile of band patterns of isozymes separated by electrophoresis that can be equated to different alleles at the DNA level.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

LIZL5: The corn plant from which seeds having ATCC Accession No. PTA-2192 were obtained, as well as plants grown from those seeds.

Phenotype: The detectable characteristics of a cell or organism, which characteristics are the manifestation of gene expression.

Quantitative Trait Loci (QTL): Genetic loci that contribute, at least in part, certain numerically representable traits that are usually continuously distributed.

Regeneration: The development of a plant from tissue culture.

SSR genetic marker profile: A profile of simple sequence repeat length polymorphisms scored by agarose gel electrophoresis following PCR™ amplification using flanking oligonucleotide primers.

Self-pollination: The transfer of pollen from the anther to the stigma of the same plant.

Single Locus Converted (Conversion) Plant: Plants which are developed by a plant breeding technique called backcrossing wherein essentially all of the desired morphological and physiological characteristics of an inbred are recovered in addition to the characteristics conferred by the single locus transferred into the inbred via the backcrossing technique. A single locus may comprise one gene, or in the case of transgenic plants, one or more transgenes integrated into the host genome at a single site (locus).

Tissue Culture: A composition comprising isolated cells of the same or a different type or a collection of such cells organized into parts of a plant.

Transgene: A genetic sequence which has been introduced into the nuclear or chloroplast genome of a maize plant by a genetic transformation technique.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

III. Inbred Corn Plant LIZL5

In accordance with one aspect of the present invention, there is provided a novel inbred corn plant, designated LIZL5. Inbred corn plant LIZL5 can be compared to inbred corn plants 01IBH2 and MM402A, which are proprietary inbreds of DEKALB Genetics Corporation. LIZL5 differs significantly (at the 1%, 5%, or 10% level) from these inbred lines in several aspects (Table 1 and Table 2).

TABLE 1

Comparison of LIZL5 with 01IBH2

| | LIZL5 | 01IBH2 | DIFF | #LOC | P VALUE |
|---|---|---|---|---|---|
| BARREN % | 1.0 | 0.5 | 0.5 | 36 | 0.69 |
| DROP % | 0.1 | 0.3 | -0.2 | 42 | 0.00** |
| EHT INCH | 29.0 | 28.8 | 0.2 | 44 | 0.37 |
| FINAL | 58.5 | 58.8 | -0.3 | 48 | 0.95 |
| MST % | 27.1 | 21.8 | 5.3 | 47 | 0.63 |
| PHT INCH | 68.6 | 64.1 | 5.4 | 44 | 0.45 |
| RTL % | 5.6 | 1.1 | 4.5 | 48 | 0.00** |
| STL % | 3.2 | 1.9 | 1.3 | 48 | 0.02* |
| YLD BU/A | 83.6 | 83.7 | -0.1 | 48 | 0.94 |

Significance Levels are indicated as: + = 10%, * = 5%, ** = 1%.
Legend Abbreviations:
BARREN % = Barren Plants (percent)
DROP % = Dropped Ears (percent)
EHT INCH = Ear Height (inches)
FINAL = Final Stand
MST % = Moisture (percent)
PHT INCH = Plant Height (inches)
RTL % = Root Lodging (percent)
STL % = Stalk Lodging (percent)
YLD BU/A = Yield (bushels/acre)

TABLE 2

Comparison of LIZL5 with MM402A

| | LIZL5 | MM402A | DIFF | #LOC | P VALUE |
|---|---|---|---|---|---|
| BARREN % | 1.0 | 2.6 | -1.6 | 21 | 0.03* |
| DROP % | 0.1 | 0.2 | 0.1 | 24 | 0.00** |
| EHT INCH | 29.0 | 24.1 | 4.9 | 23 | 0.48 |
| FINAL | 58.5 | 48.0 | 10.5 | 26 | 0.12 |
| MST % | 27.1 | 23.3 | 3.8 | 26 | 0.73 |
| PHT INCH | 68.6 | 64.9 | 3.7 | 23 | 0.24 |
| RTL % | 5.6 | 3.5 | 2.1 | 25 | 0.10 |
| STL % | 3.2 | 2.7 | 0.5 | 26 | 0.58 |
| YLD BU/A | 83.6 | 60.2 | 23.4 | 23 | 0.51 |

Significance Levels are indicated as: + = 10%, * = 5%, ** = 1%.
Legend Abbreviations:
BARREN % = Barren Plants (percent)
DROP % = Dropped Ears (percent)
EHT INCH = Ear Height (inches)
FINAL = Final Stand
MST % = Moisture (percent)
PHT INCH = Plant Height (inches)
RTL % = Root Lodging (percent)
STL % = Stalk Lodging (percent)
YLD BU/A = Yield (bushels/acre)

A. Origin and Breeding History

Inbred plant LIZL5 was derived from the 3-way cross between the line 01IBH2 and a line derived from the cross of MM402A and MM501D. The origin and breeding history of inbred plant LIZL5 can be summarized as follows:

| | |
|---|---|
| Summer 1991 | The cross between MM402A and MM501D (both proprietary DEKALB Genetics Corporation lines) was made between nursery rows MR205:15 × MR205:19. |

| | |
|---|---|
| Winter 1991–92 | The 3-way cross to 01IBH2 (a DEKALB Genetics Corporation proprietary line) was made in paired rows S26:45–46. |
| Summer 1992 | The segregating F1 was self pollinated in rows 267:21–268:21. Ear number 97 was selected. |
| Summer 1993 | The F2 ear was grown in row MR127:65. |
| Winter 1993–94 | The F3 was grown in nursery row 8N-4052. |
| Summer 1994 | The F4 was grown in row MR448:28. |
| Winter 1994–95 | The F5 was grown in row-738 and named LIZL5. |
| Summer 1995 | The F6 ear rows were grown out in rows 206:4–207;19. Row 207:9 was bulked and designated LIZL5. |

LIZL5 shows uniformity and stability within the limits of environmental influence for the traits described hereinafter in Table 3. LIZL5 has been self-pollinated and ear-rowed a sufficient number of generations with careful attention paid to uniformity of plant type to ensure homozygosity and phenotypic stability. No variant traits have been observed or are expected in LIZL5.

Inbred corn plants can be reproduced by planting the seeds of the inbred corn plant LIZL5, growing the resulting corn plants under self-pollinating or sib-pollinating conditions with adequate isolation using standard techniques well known to an artisan skilled in the agricultural arts. Seeds can be harvested from such a plant using standard, well known procedures.

B. Phenotypic Description

In accordance with another aspect of the present invention, there is provided a corn plant having the physiological and morphological characteristics of corn plant LIZL5. A description of the physiological and morphological characteristics of corn plant LIZL5 is presented in Table 3.

TABLE 3

Morphological Traits for the LIZL5 Phenotype

| | VALUE | | |
|---|---|---|---|
| CHARACTERISTIC | LIZL5 | 01IBH2 | MM402A |
| 1. STALK | | | |
| Diameter (width) cm. | 2.5 | 2.2 | 2.5 |
| Anthocyanin | Absent | Absent | Absent |
| Brace Root Color | Faint | — | Moderate |
| Nodes With Brace Roots | 1.8 | 1.0 | 1.7 |
| Internode Direction | Straight | Straight | Straight |
| Internode Length cm. | 14.2 | 13.8 | 12.7 |
| 2. LEAF | | | |
| Color | Green | Green | Dark Green |
| Length cm. | 83.6 | 33.5 | 37.8 |
| Width cm. | 8.4 | 4.2 | 4.3 |
| Sheath Anthocyanin | Absent | Absent | Absent |
| Sheath Pubescence | Moderate | Moderate | Moderate to Heavy |
| Marginal Waves | Few | Few | Few |
| Longitudinal Creases | Few | Few | Few |
| 3. TASSEL | | | |
| Length cm. | 41.1 | 35.9 | 32.7 |
| Spike Length cm. | 21.9 | 22.4 | 24.2 |
| Peduncle Length cm. | 8.6 | 7.9 | 7.1 |
| Branch Number | 6.4 | 7.9 | 1.8 |
| Anther Color | Green-Yellow | Green-Yellow | Green-Yellow |
| Glume Color | Green | Green | Green |
| Glume Band | Absent | Absent | Absent |

TABLE 3-continued

Morphological Traits for the LIZL5 Phenotype

| | VALUE | | |
|---|---|---|---|
| CHARACTERISTIC | LIZL5 | 01IBH2 | MM402A |
| 4. EAR | | | |
| Number Per Stalk | 1.2 | 1.2 | 1.0 |
| Length cm. | 15.3 | 14.2 | 17.0 |
| Shape | Semi-Conical | Semi-Conical | Semi-Conical |
| Diameter cm. | 4.7 | 4.1 | 4.2 |
| Weight gm. | 134.3 | 110.2 | 132.4 |
| Shank Length cm. | 8.1 | 9.7 | 9.4 |
| Husk Bract | Short | Short | Short |
| Husk Cover cm. | 7.0 | 4.5 | 6.0 |
| Husk Opening | Intermediate | Intermediate | Very Loose |
| Husk Color Fresh | Green | Green | Green |
| Husk Color Dry | Buff | Buff | Buff |
| Cob Diameter cm. | 3.0 | 2.4 | 2.4 |
| Cob Color | Red | Red | White |
| Shelling Percent | 87.5 | 89.3 | 88.7 |
| 5. KERNEL | | | |
| Row Number | 18.8 | 16.8 | 17.4 |
| Number Per Row | 29.9 | 28.9 | 31.7 |
| Row Direction | Slightly Curved | Slightly Curved | Slightly Curved |
| Type | Dent | Dent | Dent |
| Cap Color | Orange | Yellow | Yellow |
| Side Color | Orange | Orange | Orange |
| Length (depth) mm. | 11.5 | 11.2 | 10.8 |
| Width mm. | 8.1 | 7.4 | 7.7 |
| Thickness | 4.3 | 4.1 | 4.5 |
| Weight of 1000K gm. | 284.7 | 239.7 | 278.5 |
| Endosperm Type | Normal | Normal | Normal |
| Endosperm Color | Yellow | Yellow | Yellow |

*These are typical values. Values may vary due to environment. Other values that are substantially equivalent are also within the scope of the invention. Substantially equivalent refers to quantitative traits that when compared do not show statistical differences of their means.

C. Deposit Information

A deposit of 2500 seeds of the inbred corn plant designated LIZL5 has been made with the American Type Culture Collection (ATCC), 10801 University Blvd., Manassas, Va. on Jul. 5, 2000. Those deposited seeds have been assigned ATCC Accession No. PTA-2192. The deposit was made in accordance with the terms and provisions of the Budapest Treaty relating to deposit of microorganisms and was made for a term of at least thirty (30) years and at least five (05) years after the most recent request for the furnishing of a sample of the deposit is received by the depository, or for the effective term of the patent, whichever is longer, and will be replaced if it becomes non-viable during that period.

IV. Single Locus Conversions

When the term inbred corn plant is used in the context of the present invention, this also includes any single locus conversions of that inbred. The term single locus converted plant as used herein refers to those corn plants which are developed by a plant breeding technique called backcrossing wherein essentially all of the desired morphological and physiological characteristics of an inbred are recovered in addition to the single locus transferred into the inbred via the backcrossing technique. Backcrossing methods can be used with the present invention to improve or introduce a characteristic into the inbred. The term backcrossing as used herein refers to the repeated crossing of a hybrid progeny back to one of the parental corn plants for that inbred. The parental corn plant which contributes the locus or loci for the desired characteristic is termed the nonrecurrent or donor parent. This terminology refers to the fact that the nonrecurrent parent is used one time in the backcross protocol and therefore does not recur. The parental corn plant to which the locus or loci from the nonrecurrent parent are transferred is known as the recurrent parent as it is used for several rounds in the backcrossing protocol (Poehlman et al., 1995; Fehr, 1987; Sprague and Dudley, 1988). In a typical backcross protocol, the original inbred of interest (recurrent parent) is crossed to a second inbred (nonrecurrent parent) that carries the single locus of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the single transferred locus from the nonrecurrent parent. The backcross process may be accelerated by the use of genetic markers, such as SSR, RFLP, SNP or AFLP markers to identify plants with the greatest genetic complement from the recurrent parent.

The selection of a suitable recurrent parent is an important step for a successful backcrossing procedure. The goal of a backcross protocol is to alter or substitute a single trait or characteristic in the original inbred. To accomplish this, a single locus of the recurrent inbred is modified or substituted with the desired locus from the nonrecurrent parent, while retaining essentially all of the rest of the desired genetic, and therefore the desired physiological and morphological constitution of the original inbred. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single locus traits have been identified that are not regularly selected for in the development of a new inbred but that can be improved by backcrossing techniques. Single locus traits may or may not be transgenic; examples of these traits include, but are not limited to, male sterility, waxy starch, herbicide resistance, resistance for bacterial, fungal, or viral disease, insect resistance, male fertility, enhanced nutritional quality, industrial usage, yield stability, and yield enhancement. These genes are generally inherited through the nucleus, but may be inherited through the cytoplasm. Some known exceptions to this are genes for male sterility, some of which are inherited cytoplasmically, but still act as single locus traits. A number of exemplary single locus traits are described in, for example, PCT Application WO 95/06128, the disclosure of which is specifically incorporated herein by reference.

Examples of genes conferring male sterility include those disclosed in U.S. Pat. No. 3,861,709, U.S. Pat. No. 3,710,511, U.S. Pat. No. 4,654,465, U.S. Pat. No. 5,625,132, and U.S. Pat. No. 4,727,219, each of the disclosures of which are specifically incorporated herein by reference in their entirety. A particularly useful type of male sterility gene is one which can be induced by exposure to a chemical agent, for example, a herbicide (U.S. patent Ser. No. 08/927,368, filed Sep. 11, 1997, the disclosure of which is specifically incorporated herein by reference in its entirety). Both inducible and non-inducible male sterility genes can increase the efficiency with which hybrids are made, in that they eliminate the need to physically emasculate the corn plant used as a female in a given cross.

Where one desires to employ male-sterility systems with a corn plant in accordance with the invention, it may be beneficial to also utilize one or more male-fertility restorer genes. For example, where cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the corn plant is utilized, e.g., for silage, but in most cases, the seeds will be deemed the most valuable portion of the crop, so fertility of the hybrids in these crops must be restored. Therefore, one aspect of the current invention concerns the inbred corn plant LIZL5 comprising a single gene capable of restoring male fertility in an otherwise male-sterile inbred or hybrid plant. Examples of male-sterility genes and corresponding restorers which could be employed with the inbred of the invention are well known to those of skill in the art of plant breeding and are disclosed in, for instance, U.S. Pat. No. 5,530,191; U.S. Pat. No. 5,689,041, U.S. Pat. No. 5,741,684; and U.S. Pat. No. 5,684,242, the disclosures of which are each specifically incorporated herein by reference in their entirety.

Direct selection may be applied where a single locus acts as a dominant trait. An example of a dominant trait is the herbicide resistance trait. For this selection process, the progeny of the initial cross are sprayed with the herbicide prior to the backcrossing. The spraying eliminates any plants which do not have the desired herbicide resistance characteristic, and only those plants which have the herbicide resistance gene are used in the subsequent backcross. This process is then repeated for all additional backcross generations.

Many useful single locus traits are those which are introduced by genetic transformation techniques. Methods for the genetic transformation of maize are known to those of skill in the art. For example, methods which have been described for the genetic transformation of maize include electroporation (U.S. Pat. No. 5,384,253), electrotransformation (U.S. Pat. No. 5,371,003), microprojectile bombardment (U.S. Pat. No. 5,550,318; U.S. Pat. No. 5,736,369, U.S. Pat. No. 5,538,880; and PCT Publication WO 95/06128), *Agrobacterium*-mediated transformation (U.S. Pat. No. 5,591,616 and E.P. Publication EP672752), direct DNA uptake transformation of protoplasts (Omirulleh et al., 1993) and silicon carbide fiber-mediated transformation (U.S. Pat. No. 5,302,532 and U.S. Pat. No. 5,464,765).

A type of single locus trait which can be introduced by genetic transformation (U.S. Pat. No. 5,554,798) and has particular utility is a gene which confers resistance to the herbicide glyphosate. Glyphosate inhibits the action of the enzyme EPSPS, which is active in the biosynthetic pathway of aromatic amino acids. Inhibition of this enzyme leads to starvation for the amino acids phenylalanine, tyrosine, and tryptophan and secondary metabolites derived therefrom. Mutants of this enzyme are available which are resistant to glyphosate. For example, U.S. Pat. No. 4,535,060 describes the isolation of EPSPS mutations which confer glyphosate resistance upon organisms having the *Salmonella typhimurium* gene for EPSPS, aroA. A mutant EPSPS gene having similar mutations has also been cloned from *Zea mays*. The mutant gene encodes a protein with amino acid changes at residues 102 and 106 (PCT Publication WO 97/04103). When a plant comprises such a gene, a herbicide resistant phenotype results.

Plants having inherited a transgene comprising a mutated EPSPS gene may, therefore, be directly treated with the herbicide glyphosate without the result of significant damage to the plant. This phenotype provides farmers with the benefit of controlling weed growth in a field of plants having the herbicide resistance trait by application of the broad spectrum herbicide glyphosate. For example, one could apply the herbicide ROUNDUP™, a commercial formulation of glyphosate manufactured and sold by the Monsanto Company, over the top in fields where glyphosate resistant corn plants are grown. The herbicide application rates may typically range from 4 ounces of ROUNDUP™ to 256 ounces ROUNDUP™ per acre. More preferably, about 16 ounces to about 64 ounces per acre of ROUNDUP™ may be applied to the field. However, the application rate may be increased or decreased as needed, based on the abundance and/or type of weeds being treated. Additionally, depending on the location of the field and weather conditions, which will influence weed growth and the type of weed infestation, it may be desirable to conduct further glyphosate treatments. The second glyphosate application will also typically comprise an application rate of about 16 ounces to about 64 ounces of ROUNDUP™ per acre treated. Again, the treatment rate may be adjusted based on field conditions. Such methods of application of herbicides to agricultural crops are well known in the art and are summarized in general in Anderson (1983).

Alternatively, more than one single locus trait may be introgressed into an elite inbred by the method of backcross conversion. A selectable marker gene and a gene encoding a protein which confers a trait of interest may be simultaneously introduced into a maize plant as a result of genetic transformation. Usually one or more introduced genes will integrate into a single chromosome site in the host cell's genome. For example, a selectable marker gene encoding phosphinothricin acetyl transferase (PPT) (e.g., a bar gene) and conferring resistance to the active ingredient in some herbicides by inhibiting glutamine synthetase, and a gene encoding an endotoxin from *Bacillus thuringiensis* (Bt) and conferring resistance to particular classes of insects, e.g., lepidopteran insects, in particular the European Corn Borer, may be simultaneously introduced into a host genome. Furthermore, through the process of backcross conversion more than one transgenic trait may be transferred into an elite inbred.

The waxy characteristic is an example of a recessive trait. In this example, the progeny resulting from the first backcross generation (BC1) must be grown and selfed. A test is then run on the selfed seed from the BC1 plant to determine which BC1 plants carried the recessive gene for the waxy trait. In other recessive traits additional progeny testing, for example growing additional generations such as the BC1S1, may be required to determine which plants carry the recessive gene.

V. Origin and Breeding History of an Exemplary Single Locus Converted Plant

85DGD1 MLms is a single locus conversion of 85DGD1 to cytoplasmic male sterility. 85DGD1 MLms was derived using backcross methods. 85DGD1 (a proprietary inbred of DEKALB Genetics Corporation) was used as the recurrent parent and MLms, a germplasm source carrying ML cytoplasmic sterility, was used as the nonrecurrent parent. The breeding history of the single locus converted inbred 85DGD1 MLms can be summarized as follows:

Hawaii Nurseries Planting Date Apr. 02, 1992 Made up S-O: Female row 585 male row 500

| | |
|---|---|
| Hawaii Nurseries Planting Date Jul. 15, 1992 | S-O was grown and plants were backcrossed times 85DGD1 (rows 444' 443) |
| Hawaii Nurseries Planting Date Nov. 18, 1992 | Bulked seed of the BC1 was grown and backcrossed times 85DGD1 (rows V3-27' V3-26) |
| Hawaii Nurseries Planting Date Apr. 02, 1993 | Bulked seed of the BC2 was grown and backcrossed times 85DGD1 (rows 37' 36) |
| Hawaii Nurseries Planting Date Jul. 14, 1993 | Bulked seed of the BC3 was grown and backcrossed times 85DGD1 (rows 99' 98) |
| Hawaii Nurseries Planting Date Oct. 28, 1993 | Bulked seed of BC4 was grown and backcrossed times 85DGD1 (rows KS-63' KS-62) |
| Summer 1994 | A single ear of the BC5 was grown and backcrossed times 85DGD1 (MC94-822' MC94-822-7) |
| Winter 1994 | Bulked seed of the BC6 was grown and backcrossed times 85DGD1 (3Q-1' 3Q-2) |
| Summer 1995 | Seed of the BC7 was bulked and named 85DGD1 MLms. |

VI. Tissue Cultures and in vitro Regeneration of Corn Plants

A further aspect of the invention relates to tissue cultures of the corn plant designated LIZL5. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, kernels, ears, cobs, leaves, husks, stalks, roots, root tips, anthers, silk, and the like. In a preferred embodiment, the tissue culture comprises embryos, protoplasts, meristematic cells, pollen, leaves or anthers derived from immature tissues of these plant parts. Means for preparing and maintaining plant tissue cultures are well known in the art (U.S. Pat. No. 5,538,880; and U.S. Pat. No. 5,550,318, each incorporated herein by reference in their entirety). By way of example, a tissue culture comprising organs such as tassels or anthers has been used to produce regenerated plants (U.S. Pat. No. 5,445,961 and U.S. Pat. No. 5,322,789; the disclosures of which are incorporated herein by reference).

VII. Tassel/Anther Cultures

Tassels contain anthers which in turn enclose microspores. Microspores develop into pollen. For anther/microspore culture, if tassels are the plant composition, they are preferably selected at a stage when the microspores are uninucleate, that is, include only one, rather than 2 or 3 nuclei. Methods to determine the correct stage are well known to those skilled in the art and include mitramycin fluorescent staining (Pace et al., 1987), trypan blue (preferred) and acetocarmine squashing. The mid-uninucleate microspore stage has been found to be the developmental stage most responsive to the subsequent methods disclosed to ultimately produce plants.

Although microspore-containing plant organs such as tassels can generally be pretreated at any cold temperature below about 25° C., a range of 4 to 25° C. is preferred, and a range of 8 to 14° C. is particularly preferred. Although other temperatures yield embryoids and regenerated plants, cold temperatures produce optimum response rates compared to pretreatment at temperatures outside the preferred range. Response rate is measured as either the number of embryoids or the number of regenerated plants per number of microspores initiated in culture. Exemplary methods of microspore culture are disclosed in, for example, U.S. Pat. No. 5,322,789 and U.S. Pat. No. 5,445,961, the disclosures of which are specifically incorporated herein by reference.

Although not required, when tassels are employed as the plant organ, it is generally preferred to sterilize their surface. Following surface sterilization of the tassels, for example, with a solution of calcium hypochloride, the anthers are removed from about 70 to 150 spikelets (small portions of the tassels) and placed in a preculture or pretreatment medium. Larger or smaller amounts can be used depending on the number of anthers.

When one elects to employ tassels directly, tassels are preferably pretreated at a cold temperature for a predefined time, preferably at 10° C. for about 4 days. After pretreatment of a whole tassel at a cold temperature, dissected anthers are further pretreated in an environment that diverts microspores from their developmental pathway. The function of the preculture medium is to switch the developmental program from one of pollen development to that of embryoid/callus development. An embodiment of such an environment in the form of a preculture medium includes a sugar alcohol, for example mannitol or sorbitol, inositol or the like. An exemplary synergistic combination is the use of mannitol at a temperature of about 10° C. for a period ranging from about 10 to 14 days. In a preferred embodiment, 3 ml of 0.3 M mannitol combined with 50 mg/l of ascorbic acid, silver nitrate, and colchicine is used for incubation of anthers at 10° C. for between 10 and 14 days. Another embodiment is to substitute sorbitol for mannitol. The colchicine produces chromosome doubling at this early stage. The chromosome doubling agent is preferably only present at the preculture stage.

It is believed that the mannitol or other similar carbon structure or environmental stress induces starvation and functions to force microspores to focus their energies on entering developmental stages. The cells are unable to use, for example, mannitol as a carbon source at this stage. It is believed that these treatments confuse the cells causing them to develop as embryoids and plants from microspores. Dramatic increases in development from these haploid cells, as high as 25 embryoids in $10^4$ microspores, have resulted from using these methods.

In embodiments where microspores are obtained from anthers, microspores can be released from the anthers into an isolation medium following the mannitol preculture step. One method of rel+ease is by disruption of the anthers, for example, by chopping the anthers into pieces with a sharp instrument, such as a razor blade, scalpel, or Waring blender. The resulting mixture of released microspores, anther fragments, and isolation medium are then passed through a filter to separate microspores from anther wall fragments. An embodiment of a filter is a mesh, more specifically, a nylon mesh of about 112 mm pore size. The filtrate which results from filtering the microspore-containing solution is preferably relatively free of anther fragments, cell walls, and other debris.

In a preferred embodiment, isolation of microspores is accomplished at a temperature below about 25° C. and preferably, at a temperature of less than about 15° C. Preferably, the isolation media, dispersing tool (e.g., razor blade), funnels, centrifuge tubes, and dispersing container (e.g., petri dish) are all maintained at the reduced temperature during isolation. The use of a precooled dispersing tool to isolate maize microspores has been reported (Gaillard et al, 1991).

Where appropriate and desired, the anther filtrate is then washed several times in isolation medium. The purpose of the washing and centrifugation is to eliminate any toxic compounds which are contained in the non-microspore part of the filtrate and are created by the chopping process. The centrifugation is usually done at decreasing spin speeds, for example, 1000, 750, and finally 500 rpms. The result of the foregoing steps is the preparation of a relatively pure tissue culture suspension of microspores that are relatively free of debris and anther remnants.

To isolate microspores, an isolation media is preferred. An isolation media is used to separate microspores from the anther walls while maintaining their viability and embryogenic potential. An illustrative embodiment of an isolation media includes a 6% sucrose or maltose solution combined with an antioxidant such as 50 mg/l of ascorbic acid, 0.1 mg/l biotin, and 400 mg/l of proline, combined with 10 mg/l of nicotinic acid and 0.5 mg/l $AgNO_3$. In another embodiment, the biotin and proline are omitted.

An isolation media preferably has a higher antioxidant level where it is used to isolate microspores from a donor plant (a plant from which a plant composition containing a microspore is obtained) that is field grown in contrast to greenhouse grown. A preferred level of ascorbic acid in an isolation medium is from about 50 mg/l to about 125 mg/l and, more preferably, from about 50 mg/l to about 100 mg/l.

One can find particular benefit in employing a support for the microspores during culturing and subculturing. Any support that maintains the cells near the surface can be used. The microspore suspension is layered onto a support, for example by pipetting. There are several types of supports which are suitable and are within the scope of the invention. An illustrative embodiment of a solid support is a TRANSWELL® culture dish. Another embodiment of a solid support for development of the microspores is a bilayer plate wherein liquid media is on top of a solid base. Other embodiments include a mesh or a millipore filter. Preferably, a solid support is a nylon mesh in the shape of a raft. A raft is defined as an approximately circular support material which is capable of floating slightly above the bottom of a tissue culture vessel, for example, a petri dish, of about a 60 or 100 mm size, although any other laboratory tissue culture vessel will suffice. In an illustrative embodiment, a raft is about 55 mm in diameter.

Culturing isolated microspores on a solid support, for example, on a 10 mm pore nylon raft floating on 2.2 ml of medium in a 60 mm petri dish, prevents microspores from sinking into the liquid medium and thus avoiding low oxygen tension. These types of cell supports enable the serial transfer of the nylon raft with its associated microspore/embryoids ultimately to full strength medium containing activated charcoal and solidified with, for example, GELRITE™ (solidifying agent). The charcoal is believed to absorb toxic wastes and intermediaries. The solid medium allows embryoids to mature.

The liquid medium passes through the mesh while the microspores are retained and supported at the medium-air interface. The surface tension of the liquid medium in the petri dish causes the raft to float. The liquid is able to pass through the mesh; consequently, the microspores stay on top. The mesh remains on top of the total volume of liquid medium. An advantage of the raft is to permit diffusion of nutrients to the microspores. Use of a raft also permits transfer of the microspores from dish to dish during subsequent subculture with minimal loss, disruption, or disturbance of the induced embryoids that are developing. The rafts represent an advantage over the multi-welled TRANSWELL® plates, which are commercially available from COSTAR, in that the commercial plates are expensive. Another disadvantage of these plates is that to achieve the serial transfer of microspores to subsequent media, the membrane support with cells must be peeled off the insert in the wells. This procedure does not produce as good a yield nor as efficient transfers, as when a mesh is used as a vehicle for cell transfer.

The culture vessels can be further defined as either (1) a bilayer 60 mm petri plate wherein the bottom 2 ml of medium are solidified with 0.7% agarose overlaid with 1 ml of liquid containing the microspores; (2) a nylon mesh raft wherein a wafer of nylon is floated on 1.2 ml of medium and 1 ml of isolated microspores is pipetted on top; or (3) TRANSWELL® plates wherein isolated microspores are pipetted onto membrane inserts which support the microspores at the surface of 2 ml of medium.

After the microspores have been isolated, they are cultured in a low strength anther culture medium until about the 50 cell stage when they are subcultured onto an embryoid/callus maturation medium. Medium is defined at this stage as any combination of nutrients that permit the microspores to develop into embryoids or callus. Many examples of suitable embryoid/callus promoting media are well known to those skilled in the art. These media will typically comprise mineral salts, a carbon source, vitamins, and growth regulators. A solidifying agent is optional. A preferred embodiment of such a media is referred to as "D medium," which typically includes 6N1 salts, $AgNO_3$ and sucrose or maltose.

In an illustrative embodiment, 1 ml of isolated microspores are pipetted onto a 10 mm nylon raft and the raft is floated on 1.2 ml of medium "D," containing sucrose or preferably maltose. Both calli and embryoids can develop. Calli are undifferentiated aggregates of cells. Type I is a relatively compact, organized, and slow growing callus. Type II is a soft, friable, and fast-growing one. Embryoids are aggregates exhibiting some embryo-like structures. The embryoids are preferred for subsequent steps to regenerating plants. Culture medium "D" is an embodiment of medium that follows the isolation medium and replaces it. Medium "D" promotes growth to an embryoid/callus. This medium comprises 6N1 salts at ⅛ the strength of a basic stock solution (major components) and minor components, plus 12% sucrose, or preferably 12% maltose, 0.1 mg/l B1, 0.5 mg/l nicotinic acid, 400 mg/l proline and 0.5 mg/l silver nitrate. Silver nitrate is believed to act as an inhibitor to the action of ethylene. Multi-cellular structures of approximately 50 cells each generally arise during a period of 12 days to 3 weeks. Serial transfer after a two week incubation period is preferred.

After the petri dish has been incubated for an appropriate period of time, preferably two weeks in the dark at a predefined temperature, a raft bearing the dividing microspores is transferred serially to solid based media which promote embryo maturation. In an illustrative embodiment, the incubation temperature is 30° C. and the mesh raft supporting the embryoids is transferred to a 100 mm petri dish containing the 6N1-TGR-4P medium, an "anther culture medium." This medium contains 6N1 salts, supplemented with 0.1 mg/l TIBA, 12% sugar (sucrose, maltose, or a combination thereof), 0.5% activated charcoal, 400 mg/l proline, 0.5 mg/l B, 0.5 mg/l nicotinic acid, and 0.2 percent GELRITE™ (solidifying agent) and is capable of promoting the maturation of the embryoids. Higher quality embryoids, that is, embryoids which exhibit more organized development, such as better shoot meristem formation without precocious germination, were typically obtained with the transfer to full strength medium compared to those resulting from continuous culture using only, for example, the isolated microspore culture (IMC) Medium "D." The maturation process permits the pollen embryoids to develop further in route toward the eventual regeneration of plants. Serial transfer occurs to full strength solidified 6N1 medium using either the nylon raft, the TRANSWELL® membrane, or bilayer plates, each one requiring the movement of developing embryoids to permit further development into physiologically more mature structures. In an especially preferred embodiment, microspores are isolated in an isolation media comprising about 6% maltose, cultured for about two weeks in an embryoid/calli induction medium comprising about 12% maltose and then transferred to a solid medium comprising about 12% sucrose.

At the point of transfer of the raft, after about two weeks of incubation, embryoids exist on a nylon support. The purpose of transferring the raft with the embryoids to a solidified medium after the incubation is to facilitate embryo maturation. Mature embryoids at this point are selected by visual inspection indicated by zygotic embryo-like dimensions and structures and are transferred to the shoot initiation medium. It is preferred that shoots develop before roots, or that shoots and roots develop concurrently. If roots develop before shoots, plant regeneration can be impaired. To produce solidified media, the bottom of a petri dish of approximately 100 mm is covered with about 30 ml of 0.2% GELRITE™ solidified medium. A sequence of regeneration media are used for whole plant formation from the embryoids.

During the regeneration process, individual embryoids are induced to form plantlets. The number of different media in the sequence can vary depending on the specific protocol used. Finally, a rooting medium is used as a prelude to transplanting to soil. When plantlets reach a height of about 5 cm, they are then transferred to pots for further growth into flowering plants in a greenhouse by methods well known to those skilled in the art.

Plants have been produced from isolated microspore cultures by the methods disclosed herein, including self-pollinated plants. The rate of embryoid induction was much higher with the synergistic preculture treatment consisting of a combination of stress factors, including a carbon source which can be capable of inducing starvation, a cold temperature, and colchicine, than has previously been reported. An illustrative embodiment of the synergistic combination of treatments leading to the dramatically improved response rate compared to prior methods, is a temperature of about 10° C., mannitol as a carbon source, and 0.05% colchicine.

The inclusion of ascorbic acid, an anti-oxidant, in the isolation medium is preferred for maintaining good microspore viability. However, there seems to be no advantage to including mineral salts in the isolation medium. The osmotic potential of the isolation medium was maintained optimally with about 6% sucrose, although a range of 2% to 12% is within the scope of this invention.

In an embodiment of the embryoid/callus organizing media, mineral salts concentration in IMC Culture Media "D" is (⅛×), the concentration which is used also in anther culture medium. The 6N1 salts major components have been modified to remove ammonium nitrogen. Osmotic potential in the culture medium is maintained with about 12% sucrose and about 400 mg/l proline. Silver nitrate (0.5 mg/l) was included in the medium to modify ethylene activity. The preculture media is further characterized by having a pH of about 5.7 to 6.0. Silver nitrate and vitamins do not appear to be crucial to this medium but do improve the efficiency of the response.

Whole anther cultures can also be used in the production of monocotyledonous plants from a plant culture system. There are some basic similarities of anther culture methods and microspore culture methods with regard to the media used. A difference from isolated microspore cultures is that undisrupted anthers are cultured, so that a support, e.g., a nylon mesh support, is not needed. The first step in developing the anther cultures is to incubate tassels at a cold temperature. A cold temperature is defined as less than about 25° C. More specifically, the incubation of the tassels is preferably performed at about 10° C. A range of 8 to 14° C. is also within the scope of the invention. The anthers are then dissected from the tassels, preferably after surface sterilization using forceps, and placed on solidified medium. An example of such a medium is designated 6N1-TGR-P4.

The anthers are then treated with environmental conditions that are combinations of stresses that are capable of diverting microspores from gametogenesis to embryogenesis. It is believed that the stress effect of sugar alcohols in the preculture medium, for example, mannitol, is produced by inducing starvation at the predefined temperature. In one embodiment, the incubation pretreatment is for about 14 days at 10° C. It was found that treating the anthers in addition with a carbon structure, an illustrative embodiment being a sugar alcohol, preferably mannitol, produces dramatically higher anther culture response rates as measured by the number of eventually regenerated plants, than by treatment with either cold treatment or mannitol alone. These results are particularly surprising in light of teachings that cold is better than mannitol for these purposes, and that warmer temperatures interact with mannitol better.

To incubate the anthers, they are floated on a preculture medium which diverts the microspores from gametogenesis, preferably on a mannitol carbon structure, more specifically, 0.3 M of mannitol plus 50 mg/l of ascorbic acid. Three milliliters is about the total amount in a dish, for example, a tissue culture dish, more specifically, a 60 mm petri dish. Anthers are isolated from about 120 spikelets for one dish yields about 360 anthers.

Chromosome doubling agents can be used in the preculture media for anther cultures. Several techniques for doubling chromosome number (Jensen, 1974; Wan et al., 1989) have been described. Colchicine is one of the doubling agents. However, developmental abnormalities arising from in vitro cloning are further enhanced by colchicine treatments, and previous reports indicated that colchicine is toxic to microspores. The addition of colchicine in increasing concentrations during mannitol pretreatment prior to anther culture and microspore culture has achieved improved percentages.

An illustrative embodiment of the combination of a chromosome doubling agent and preculture medium is one which contains colchicine. In a specific embodiment, the colchicine level is preferably about 0.05%. The anthers remain in the mannitol preculture medium with the additives for about 10 days at 10° C. Anthers are then placed on maturation media, for example, that designated 6N1-TGR-P4, for 3 to 6 weeks to induce embryoids. If the plants are to be regenerated from the embryoids, shoot regeneration medium is employed, as in the isolated microspore procedure described in the previous sections. Other regeneration media can be used sequentially to complete regeneration of whole plants.

The anthers are then exposed to embryoid/callus promoting medium, for example, that designated 6N1-TGR-P4, to obtain callus or embryoids. The embryoids are recognized visually by identification of embryonic-like structures. At this stage, the embryoids are transferred progressively through a series of regeneration media. In an illustrative embodiment, the shoot initiation medium comprises BAP (6-benzyl-amino-purine) and NAA (naphthalene acetic acid). Regeneration protocols for isolated microspore cultures and anther cultures are similar.

VIII. Additional Tissue Cultures and Regeneration

The present invention contemplates a corn plant regenerated from a tissue culture of the inbred maize plant LIZL5, or of a hybrid maize plant produced by crossing LIZL5. As is well known in the art, tissue culture of corn can be used for the in vitro regeneration of a corn plant. By way of example, a process of tissue culturing and regeneration of corn is described in European Patent Application 0 160 390, the disclosure of which is incorporated herein by reference. Corn tissue culture procedures are also described in Green and Rhodes (1982) and Duncan et al (1985). The study by Duncan et al (1985) indicates that 97 percent of cultured plants produced calli capable of regenerating plants. Subsequent studies have shown that both inbreds and hybrids produced 91% regenerable calli that produced plants.

Other studies indicate that non-traditional tissues are capable of producing somatic embryogenesis and plant regeneration (Songstad et at, 1988; Rao et al, 1986; Conger et al., 1987; the disclosures of which are incorporated herein by reference). Regenerable cultures, including Type I and Type II cultures, may be initiated from immature embryos using methods described in, for example, PCT Application WO 95/06128, the disclosure of which is incorporated herein by reference in its entirety.

Briefly, by way of example, to regenerate a plant of this invention, cells are selected following growth in culture. Where employed, cultured cells are preferably grown either on solid supports or in the form of liquid suspensions as set forth above. In either instance, nutrients are provided to the cells in the form of media, and environmental conditions are controlled. There are many types of tissue culture media comprising amino acids, salts, sugars, hormones, and vitamins. Most of the media employed to regenerate inbred and hybrid plants have some similar components; the media differ in the composition and proportions of their ingredients depending on the particular application envisioned. For example, various cell types usually grow in more than one type of media, but exhibit different growth rates and different morphologies, depending on the growth media. In some media, cells survive but do not divide. Various types of media suitable for culture of plant cells have been previously described and discussed above.

An exemplary embodiment for culturing recipient corn cells in suspension cultures includes using embryogenic cells in Type II (Armstrong and Green, 1985; Gordon-Kamm et al., 1990) callus, selecting for small (10 to 30 mm)

isodiametric, cytoplasmically dense cells, growing the cells in suspension cultures with hormone containing media, subculturing into a progression of media to facilitate development of shoots and roots, and finally, hardening the plant and readying it metabolically for growth in soil.

Meristematic cells (i.e., plant cells capable of continual cell division and characterized by an undifferentiated cytological appearance, normally found at growing points or tissues in plants such as root tips, stem apices, lateral buds, etc.) can be cultured (U.S. Pat. No. 5,736,369, the disclosure of which is specifically incorporated herein by reference).

Embryogenic calli are produced essentially as described in PCT Application WO 95/06128. Specifically, inbred plants or plants from hybrids produced from crossing an inbred of the present invention with another inbred are grown to flowering in a greenhouse. Explants from at least one of the following $F_1$ tissues: the immature tassel tissue, intercalary meristems and leaf bases, apical meristems, immature ears and immature embryos are placed in an initiation medium which contain MS salts, supplemented with thiamine, agar, and sucrose. Cultures are incubated in the dark at about 23° C. All culture manipulations and selections are performed with the aid of a dissecting microscope.

After about 5 to 7 days, cellular outgrowths are observed from the surface of the explants. After about 7 to 21 days, the outgrowths are subcultured by placing them into fresh medium of the same composition. Some of the intact immature embryo explants are placed on fresh medium. Several subcultures later (after about 2 to 3 months) enough material is present from explants for subdivision of these embryogenic calli into two or more pieces.

Callus pieces from different explants are not mixed. After further growth and subculture (about 6 months after embryogenic callus initiation), there are usually between 1 and 100 pieces derived ultimately from each selected explant. During this time of culture expansion, a characteristic embryogenic culture morphology develops as a result of careful selection at each subculture. Any organized structures resembling roots or root primordia are discarded. Material known from experience to lack the capacity for sustained growth is also discarded (translucent, watery, embryogenic structures). Structures with a firm consistency resembling at least in part the scutelum of the in vivo embryo are selected.

The callus is maintained on agar-solidified MS or N6-type media. A preferred hormone is 2,4-D. A second preferred hormone is dicamba. Visual selection of embryo-like structures is done to obtain subcultures. Transfer of material other than that displaying embryogenic morphology results in loss of the ability to recover whole plants from the callus.

Cell suspensions are prepared from the calli by selecting cell populations that appear homogeneous macroscopically. A portion of the friable, rapidly growing embryogenic calli is inoculated into MS or N6 Medium containing 2,4-D or dicamba. The calli in medium are incubated at about 27° C. on a gyrotary shaker in the dark or in the presence of low light. The resultant suspension culture is transferred about once every three to seven days, preferably every three to four days, by taking about 5 to 10 ml of the culture and introducing this inoculum into fresh medium of the composition listed above (PCT Application WO 95/06128).

For regeneration of type I or type II callus, callus is transferred to a solidified culture medium which includes a lower concentration of 2,4-D or other auxins than is present in culture medium used for callus maintenance (PCT Application WO 95/06128, specifically incorporated herein by reference). Other hormones which can be used in regeneration media include dicamba, NAA, ABA, BAP, and 2-NCA. Regeneration of plants is completed by the transfer of mature and germinating embryos to a hormone-free medium, followed by the transfer of developed plantlets to soil and growth to maturity. Plant regeneration is described in PCT Application WO 95/06128.

Cells from the meristem or cells fated to contribute to the meristem of a cereal plant embryo at the early proembryo, mid proembryo, late proembryo, transitional or early coleoptilar stage may be cultured so as to produce a proliferation of shoots or multiple meristems from which fertile plants may be regenerated. Alternatively, cells from the meristem or cells fated to contribute to the meristem of a cereal plant immature ear or tassel may be cultured so as to produce a proliferation of shoots or multiple meristems from which fertile plants may be regenerated (U.S. Pat. No. 5,736,369).

Progeny of any generation are produced by taking pollen and selfing, backcrossing, or sibling crossing regenerated plants by methods well known to those skilled in the arts. Seeds are collected from the regenerated plants. Alternatively, progeny of any generation may be produced by pollinating a regenerated plant with its own pollen or pollen of a second maize plant. Using the methods described herein, tissue cultures and immature or mature plant tissues may be used as recipient cell cultures for the process of genetic transformation.

IX. Processes of Preparing Corn Plants and the Corn Plants Produced by Such Crosses The present invention also provides a process of preparing a novel corn plant and a corn plant produced by such a process. In accordance with such a process, a first parent corn plant is crossed with a second parent corn plant wherein at least one of the first and second corn plants is the inbred corn plant LIZL5. An important aspect of this process is that it can be used for the development of novel inbred lines. For example, the inbred corn plant LIZL5 could be crossed to any second plant, and the resulting hybrid progeny each selfed for about 5 to 7 or more generations, thereby providing a large number of distinct, pure-breeding inbred lines. These inbred lines could then be crossed with other inbred or non-inbred lines and the resulting hybrid progeny analyzed for beneficial characteristics. In this way, novel inbred lines conferring desirable characteristics could be identified.

In selecting a second plant to cross with LIZL5 for the purpose of developing novel inbred lines, it will typically be desired choose those plants which either themselves exhibit one or more selected desirable characteristics or which exhibit the desired characteristic(s) when in hybrid combination. Examples of potentially desired characteristics include greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size. Alternatively, the inbred LIZL5 may be crossed with a second, different inbred plant for the purpose of producing hybrid seed which is sold to farmers for planting in commercial production fields. In this case, a second inbred variety is selected which confers desirable characteristics when in hybrid combination with the first inbred line.

Corn plants (*Zea mays* L.) can be crossed by either natural or mechanical techniques. Natural pollination occurs in corn when wind blows pollen from the tassels to the silks that protrude from the tops of the recipient ears. Mechanical pollination can be effected either by controlling the types of pollen that can blow onto the silks or by pollinating by hand.

In a preferred embodiment, crossing comprises the steps of:

(a) planting in pollinating proximity seeds of a first and a second parent corn plant, and preferably, seeds of a first inbred corn plant and a second, distinct inbred corn plant;

(b) cultivating or growing the seeds of the first and second parent corn plants into plants that bear flowers;

(c) emasculating flowers of either the first or second parent corn plant, i.e., treating the flowers so as to prevent pollen production, or alternatively, using as the female parent a male sterile plant, thereby providing an emasculated parent corn plant;

(d) allowing natural cross-pollination to occur between the first and second parent corn plants;

(e) harvesting seeds produced on the emasculated parent corn plant; and, where desired, (f) growing the harvested seed into a corn plant, preferably, a hybrid corn plant.

Parental plants are typically planted in pollinating proximity to each other by planting the parental plants in alternating rows, in blocks or in any other convenient planting pattern. Where the parental plants differ in timing of sexual maturity, it may be desired to plant the slower maturing plant first, thereby ensuring the availability of pollen from the male parent during the time at which silks on the female parent are receptive to pollen. Plants of both parental parents are cultivated and allowed to grow until the time of flowering. Advantageously, during this growth stage, plants are in general treated with fertilizer and/or other agricultural chemicals as considered appropriate by the grower.

At the time of flowering, in the event that plant LIZL5 is employed as the male parent, the tassels of the other parental plant are removed from all plants employed as the female parental plant to avoid self-pollination. The detasseling can be achieved manually but also can be done by machine, if desired. Alternatively, when the female parent corn plant comprises a cytoplasmic or nuclear gene conferring male sterility, detasseling may not be required. Additionally, a chemical gametocide may be used to sterilize the male flowers of the female plant. In this case, the parent plants used as the male may either not be treated with the chemical agent or may comprise a genetic factor which causes resistance to the emasculating effects of the chemical agent. Gametocides affect processes or cells involved in the development, maturation or release of pollen. Plants treated with such gametocides are rendered male sterile, but typically remain female fertile. The use of chemical gametocides is described, for example, in U.S. Pat. No. 4,936,904, the disclosure of which is specifically incorporated herein by reference in its entirety. Furthermore, the use of Roundup herbicide in combination with glyphosate tolerant maize plants to produce male sterile corn plants is disclosed in U.S. patent application Ser. No. 08/927,368 and PCT Publication WO 98/44140.

Following emasculation, the plants are then typically allowed to continue to grow and natural cross-pollination occurs as a result of the action of wind, which is normal in the pollination of grasses, including corn. As a result of the emasculation of the female parent plant, all the pollen from the male parent plant is available for pollination because tassels, and thereby pollen bearing flowering parts, have been previously removed from all plants of the inbred plant being used as the female in the hybridization. Of course, during this hybridization procedure, the parental varieties are grown such that they are isolated from other corn fields to minimize or prevent any accidental contamination of pollen from foreign sources. These isolation techniques are well within the skill of those skilled in this art.

Both parental inbred plants of corn may be allowed to continue to grow until maturity or the male rows may be destroyed after flowering is complete. Only the ears from the female inbred parental plants are harvested to obtain seeds of a novel $F_1$ hybrid. The novel $F_1$ hybrid seed produced can then be planted in a subsequent growing season in commercial fields or, alternatively, advanced in breeding protocols for purposes of developing novel inbred lines.

Alternatively, in another embodiment of the invention, both first and second parent corn plants can come from the same inbred corn plant, i.e., from the inbred designated LIZL5. Thus, any corn plant produced using a process of the present invention and inbred corn plant LIZL5, is contemplated by the current inventor. As used herein, crossing can mean selfing, backcrossing, crossing to another or the same inbred, crossing to populations, and the like. All corn plants produced using the inbred corn plant LIZL5 as a parent are, therefore, within the scope of this invention.

The utility of the inbred plant LIZL5 also extends to crosses with other species. Commonly, suitable species will be of the family Graminaceae, and especially of the genera *Zea*, *Tripsacum*, *Coix*, *Schlerachne*, *Polytoca*, *Chionachne*, and *Trilobachne*, of the tribe Maydeae. Of these, *Zea* and *Tripsacum*, are most preferred. Potentially suitable for crosses with LIZL5 can also be the various varieties of grain sorghum, *Sorghum bicolor* (L.) Moench.

A. $F_1$ Hybrid Corn Plant and Seed Production

Any time the inbred corn plant LIZL5 is crossed with another, different, corn inbred, a first generation ($F_1$) corn hybrid plant is produced. As such, an $F_1$ hybrid corn plant may be produced by crossing LIZL5 with any second inbred maize plant. Therefore, any $F_1$ hybrid corn plant or corn seed which is produced with LIZL5 as a parent is part of the present invention. An example of such an $F_1$ hybrid which has been produced with LIZL5 as a parent is the hybrid 7026255. Hybrid 7026255 was produced by crossing inbred corn plant LIZL5 with the inbred corn plant designated 16SCQ2.

The goal of the process of producing an $F_1$ hybrid is to manipulate the genetic complement of corn to generate new combinations of genes which interact to yield new or improved traits (phenotypic characteristics). A process of producing an $F_1$ hybrid typically begins with the production of one or more inbred plants. Those plants are produced by repeated crossing of ancestrally related corn plants to try to combine certain genes within the inbred plants.

Corn has a diploid phase which means two conditions of a gene (two alleles) occupy each locus (position on a chromosome). If the alleles are the same at a locus, there is said to be homozygosity. If they are different, there is said to be heterozygosity. In a completely inbred plant, all loci are homozygous. Because many loci when homozygous are deleterious to the plant, in particular leading to reduced vigor, less kernels, weak and/or poor growth, production of inbred plants is an unpredictable and arduous process. Under some conditions, heterozygous advantage at some loci effectively bars perpetuation of homozygosity.

Inbreeding requires sophisticated manipulation by human breeders. Even in the extremely unlikely event inbreeding rather than crossbreeding occurred in natural corn, achievement of complete inbreeding cannot be expected in nature due to well known deleterious effects of homozygosity and the large number of generations the plant would have to breed in isolation. The reason for the breeder to create inbred plants is to have a known reservoir of genes whose gametic transmission is predictable.

The development of inbred plants generally requires at least about 5 to 7 generations of selfing. Inbred plants are then cross-bred in an attempt to develop improved $F_1$ hybrids. Hybrids are then screened and evaluated in small scale field trials. Typically, about 10 to 15 phenotypic traits, selected for their potential commercial value, are measured. A selection index of the most commercially important traits is used to help evaluate hybrids. FACT, an acronym for Field Analysis Comparison Trial (strip trials), is an on-farm experimental testing program employed by DEKALB Genetics Corporation to perform the final evaluation of the commercial potential of a product.

During the next several years, a progressive elimination of hybrids occurs based on more detailed evaluation of their phenotype. Eventually, strip trials (FACT) are conducted to formally compare the experimental hybrids being developed with other hybrids, some of which were previously developed and generally are commercially successful. That is, comparisons of experimental hybrids are made to competitive hybrids to determine if there was any advantage to further development of the experimental hybrids. Examples of such comparisons are presented hereinbelow. After FACT testing is complete, determinations may be made whether commercial development should proceed for a given hybrid.

When the inbred corn plant LIZL5 is crossed with another inbred plant to yield a hybrid, the original inbred can serve as either the maternal or paternal plant. For many crosses, the outcome is the same regardless of the assigned sex of the parental plants.

However, there is often one of the parental plants that is preferred as the maternal plant because of increased seed yield and production characteristics. Some plants produce tighter ear husks leading to more loss, for example due to rot. There can be delays in silk formation which deleteriously affect timing of the reproductive cycle for a pair of parental inbreds. Seed coat characteristics can be preferable in one plant. Pollen can be shed better by one plant. Other variables can also affect preferred sexual assignment of a particular cross. In the case of the instant inbred, LIZL5 could be used as the male or female parent in hybrid crosses. In certain embodiments of the invention, it may be desired to use LIZL5 as the male parent.

B. $F_1$ Hybrid Comparisons

As mentioned above, hybrids are progressively eliminated following detailed evaluations of their phenotype, including formal comparisons with other commercially successful hybrids. Strip trials are used to compare the phenotypes of hybrids grown in as many environments as possible. They are performed in many environments to assess overall performance of the new hybrids and to select optimum growing conditions. Because the corn is grown in close proximity, environmental factors that affect gene expression, such as moisture, temperature, sunlight, and pests, are minimized. For a decision to be made to commercialize a hybrid, it is not necessary that the hybrid be better than all other hybrids. Rather, significant improvements must be shown in at least some traits that would create improvements in some niches.

Examples of such comparative data are set forth hereinbelow in Table 4, which presents a comparison of performance data for the hybrid 7026255, a hybrid made with LIZL5 as one parent, versus selected hybrids of commercial value (DK679, DK658 and DK655).

All the data in Table 4 represents results across years and locations for research and/or strip trials. The "NTEST" represents the number of paired observations in designated tests at locations around the United States.

TABLE 4

Comparative Data of 7026255

| HYBRID | NTEST | SI % C | YLD BU | MST PTS | STL % | RTL % | DRP % | FLSTD % M | SV RAT | ELSTD % M | PHT INCH | EHT INCH | BAR % | SG RAT | TST LBS | FGDU | ESTR DAYS |
|---|---|---|---|---|---|---|---|---|---|---|---|---|---|---|---|---|---|
| 706255 | R 193 | 103.9 | 180.1 | 23.6 | 2.8 | 4.4 | 0.6 | 100.7 | 3.3 | 101.1 | 99.4 | 47.8 | 1.6 | 3.8 | 55.3 | 1430 | 116.1 |
| DK679 | | 103.2 | 180.6 | 23.2 | 4.1 | 5.5 | 0.1 | 100.0 | 3.6 | 100.2 | 99.9 | 49.7 | 1.0 | 4.6 | 58.2 | 1477 | 116.0 |
| DIFF | | 0.6 | −0.5 | 0.4 | −1.3 | −1.1 | 0.5 | 0.8 | −0.4 | 0.8 | −0.5 | −1.9 | 0.5 | −0.8 | −3.0 | −47 | 0.1 |
| SIG | | | | * | * | | + | * | | | | | | ** | ** | ** | |
| 7026255 | R 193 | 103.9 | 179.8 | 23.6 | 2.7 | 4.4 | 0.6 | 100.7 | 3.2 | 101.1 | 99.4 | 48.0 | 1.6 | 3.8 | 55.3 | 1433 | 116.1 |
| DK658 | | 95.6 | 163.8 | 20.2 | 2.5 | 5.3 | 0.2 | 100.7 | 3.6 | 101.1 | 95.5 | 42.1 | 1.2 | 4.9 | 57.6 | 1416 | 113.7 |
| DIFF | | 8.3 | 16.0 | 3.5 | 0.2 | −0.9 | 0.4 | 0.0 | −0.4 | 0.0 | 4.0 | 5.9 | 0.4 | −1.1 | −2.3 | 17 | 2.4 |
| SIG | | ** | ** | ** | | | | | + | ** | ** | ** | | ** | ** | * | ** |
| 7026255 | R 110 | 100.2 | 184.1 | 23.8 | 3.0 | 7.6 | 0.2 | 100.9 | 3.2 | 101.4 | 99.8 | 48.0 | 1.7 | 3.8 | 55.6 | 1446 | 116.0 |
| DK655 | | 100.6 | 178.6 | 20.4 | 3.4 | 7.5 | 0.0 | 98.5 | 3.8 | 95.0 | 92.1 | 43.3 | 1.1 | 5.9 | 58.7 | 1443 | 113.9 |
| DIFF | | −0.4 | 5.5 | 3.4 | −0.4 | 0.1 | 0.2 | 2.4 | −0.6 | 6.4 | 7.7 | 4.6 | 0.6 | −2.1 | −3.1 | 3 | 2.1 |
| SIG | | | * | ** | | | | ** | ** | ** | ** | ** | | ** | ** | | ** |

Significance levels are indicated as: + = 10%, * = 5%, ** = 1%
LEGEND ABBREVIATIONS:
HYBD = Hybrid
NTEST = Research/FACT
SI % C = Selection Index (percent of check)
YLD BU/A = Yield (bushels/acre)
MST PTS = Moisture
STL % = Stalk Lodging (percent)
RTL % = Root Lodging (percent)
DRP % = Dropped Ears (percent)
FLSTD % M = Final Stand (percent of test mean)
SV RAT = Seedling Vigor Rating
ELSTD % M = Early Stand (percent of test mean)
PHT INCH = Plant Height (inches)
EHT INCH = Ear Height (inches)
BAR % = Barren Plants (percent)
SG RAT = Staygreen Rating
TST LBS = Test Weight (pounds)
FGDU = GDUs to Shed
ESTR DAYS = Estimated Relative Maturity (days)

As can be seen in Table 4, the hybrid 7026255 differs significantly in a number of traits when compared to successful commercial hybrids.

C. Physical Description of $F_1$ Hybrids

The present invention provides $F_1$ hybrid corn plants derived from the corn plant LIZL5. The physical characteristics of an exemplary hybrid produced using LIZL5 as one inbred parent are set forth in Table 5, which concerns hybrid corn plant 7026255. An explanation of terms used in Table 5 can be found in the Definitions, set forth hereinabove.

TABLE 5

Morphological Traits for the 7026255 Phenotype

| CHARACTERISTIC | VALUE |
| --- | --- |
| 1. STALK | |
| Diameter (width) cm. | 1.9 |
| Nodes With Brace Roots | 1.0 |
| Internode Direction | Zig-Zag |
| Internode Length cm. | 17.6 |
| 2. LEAF | |
| Color | Green |
| Length cm. | 70.5 |
| Width cm. | 7.6 |
| Sheath Pubescence | Heavy |
| Marginal Waves | Few |
| Longitudinal Creases | Few |
| 3. TASSEL | |
| Length cm. | 37.3 |
| Spike Length cm. | 17.3 |
| Peduncle Length cm. | 11.9 |
| Branch Number | 5.8 |
| Anther Color | Tan |
| Glume Color | Green |
| Glume Band | Absent |
| 4. EAR | |
| Silk Color | pink |
| Number Per Stalk | 1.0 |
| Length cm. | 15.2 |
| Shape | Semi-Conical |
| Diameter cm. | 4.6 |
| Weight gin. | 118.0 |
| Shank Length cm. | 3.9 |
| Husk Bract | Short |
| Husk Cover cm. | 5.6 |
| Husk Opening | Intermediate |
| Husk Color Fresh | Green |
| Husk Color Dry | Buff |
| Cob Diameter cm. | 2.6 |
| Cob Color | Red |
| Shelling Percent | 88.3 |
| 5. KERNEL | |
| Row Number | 16.4 |
| Number Per Row | 30.0 |
| Row Direction | Slightly Curved |
| Type | Dent |
| Cap Color | Orange |
| Side Color | Orange |
| Length (depth) mm. | 12.0 |
| Width mm. | 8.2 |
| Thickness | 4.0 |
| Weight of 1000K gm. | 312.5 |
| Endosperm Type | Normal |
| Endosperm Color | Yellow |

*These are typical values. Values may vary due to environment. Other values that are substantially equivalent are also within the scope of the invention. Substantially equivalent refers to quantitative traits that when compared do not show statistical differences of their means.

X. Genetic Complements

The present invention provides a genetic complement of the inbred corn plant designated LIZL5. Further provided by the invention is a hybrid genetic complement, wherein the complement is formed by the combination of a haploid genetic complement from LIZL5 and another haploid genetic complement. Means for determining such a genetic complement are well-known in the art.

As used herein, the phrase "genetic complement" means an aggregate of nucleotide sequences, the expression of which defines the phenotype of a corn plant or a cell or tissue of that plant. By way of example, a corn plant is genotyped to determine a representative sample of the inherited markers it possesses. Markers are alleles at a single locus. They are preferably inherited in codominant fashion so that the presence of both alleles at a diploid locus is readily detectable, and they are free of environmental variation, i.e., their heritability is 1. This genotyping is preferably performed on at least one generation of the descendant plant for which the numerical value of the quantitative trait or traits of interest are also determined. The array of single locus genotypes is expressed as a profile of marker alleles, two at each locus. The marker allelic composition of each locus can be either homozygous or heterozygous. Homozygosity is a condition where both alleles at a locus are characterized by the same nucleotide sequence or size of a repeated sequence. Heterozygosity refers to different conditions of the gene at a locus. A preferred type of genetic marker for use with the invention is simple sequence repeats (SSRs), although potentially any other type of genetic marker could be used, for example, restriction fragment length polymorphisms (RFLPs), amplified fragment length polymorphisms (AFLPs), single nucleotide polymorphisms (SNPs), and isozymes.

A genetic marker profile of an inbred may be predictive of the agronomic traits of a hybrid produced using that inbred. For example, if an inbred of known genetic marker profile and phenotype is crossed with a second inbred of known genetic marker profile and phenotype it is possible to predict the phenotype of the $F_1$ hybrid based on the combined genetic marker profiles of the parent inbreds. Methods for prediction of hybrid performance from genetic marker data is disclosed in U.S. Pat. No. 5,492,547, the disclosure of which is specifically incorporated herein by reference in its entirety. Such predictions may be made using any suitable genetic marker, for example, SSRs, RFLPs, AFLPs, SNPs, or isozymes.

SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR™), thereby eliminating the need for labor-intensive Southern hybridization. The PCR™ detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology. Following amplification, markers can be scored by gel electrophoresis of the amplification products. Scoring of marker genotype is based on the size (number of base pairs) of the amplified segment.

Means for performing genetic analyses using SSR polymorphisms are well known in the art. The SSR analyses reported herein were conducted by Celera AgGen in Davis, CA. This service is available to the public on a contractual basis. This analysis was carried out by amplification of simple repeats followed by detection of marker genotypes using gel electrophoresis. Markers were scored based on the size of the amplified fragment.

The SSR genetic marker profile of the parental inbreds and exemplary resultant hybrid described herein were determined. Because an inbred is essentially homozygous at all relevant loci, an inbred should, in almost all cases, have only one allele at each locus. In contrast, a diploid genetic marker profile of a hybrid should be the sum of those parents, e.g., if one inbred parent had the allele 168 (base pairs) at a particular locus, and the other inbred parent had 172, the hybrid is 168.172 by inference. Subsequent generations of progeny produced by selection and breeding are expected to be of genotype 168, 172, or 168.172 for that locus position. When the $F_1$ plant is used to produce an inbred, the locus should be either 168 or 172 for that position. Surprisingly, it has been observed that in certain instances, novel SSR genotypes arise during the breeding process. For example, a genotype of 170 may be observed at a particular locus position from the cross of parental inbreds with 168 and 172 at that locus. Such a novel SSR genotype may further define an inbred from the parental inbreds from which it was derived. An SSR genetic marker profile of LIZL5 is presented in Table 6.

TABLE 6

SSR Profile of LIZL5 and Comparative Inbreds

| LOCUS | LIZL5 | 01IBH2 | MM402A |
|---|---|---|---|
| BNGL105 | 92 | 92 | 106 |
| BNGL118 | 110 | 110 | 110 |
| BNGL149 | 183 | — | — |
| BNGL244 | 145 | 145 | 158 |
| BNGL252 | 164 | 164 | — |
| BNGL426 | 119 | — | — |
| BNGL589 | 175 | 175 | 156 |
| BNGL615 | 194 | 231 | 194 |
| BNGL619 | 275 | — | 269 |
| DUP14 | 76 | — | 76 |
| DUP28 | 131 | — | 123 |
| MC1014 | 163 | 163 | 169 |
| MC1017 | 196 | 196 | 198 |
| MC1018 | 140 | — | 140 |
| MC1022 | 116 | — | 116 |
| MC1043 | 165 | — | 165 |
| MC1065 | 219 | 219 | 219 |
| MC1070 | 239 | — | 239 |
| MC1074 | 164 | — | 180 |
| MC1094 | 170 | — | 170 |
| MC1129 | 204 | 204 | 198 |
| MC1138 | 188 | — | 188 |
| MC1176 | 220 | 220 | 248 |
| MC1189 | 225 | 227 | 225 |
| MC1191 | 213 | 213 | 207 |
| MC1194 | 143 | 143 | 143 |
| MC1208 | 111 | 111 | 115 |
| MC1209 | 184 | 184 | 180 |
| MC1237 | 159 | 159 | 159 |
| MC1257 | 180 | — | 179 |
| MC1265 | 220 | — | 244 |
| MC1287 | 160 | 160 | 158 |
| MC1305 | 160 | 160 | 160 |
| MC1325 | 171 | 171 | 171 |
| MC1329 | 95 | — | 93 |
| MC1371 | 95 | 134 | 95 |
| MC1449 | 95 | 95 | 95 |
| MC1456 | 176 | 187 | 176 |
| MC1484 | 124 | 124 | 124 |
| MC1520 | 299 | 275 | 299 |
| MC1523 | 199 | 199 | 199 |
| MC1538 | 213 | — | 213 |
| MC1605 | 110 | — | 110 |
| MC1662 | 151 | 161 | 167 |
| MC1740 | 129 | — | — |
| MC1782 | 228 | 228 | — |
| MC1784 | 254 | 254 | 252 |
| MC1831 | 182 | 184 | — |
| MC1839 | 186 | 186 | 186 |
| MC1890 | 163 | — | 142 |
| MC1904 | 191 | — | 170 |
| MC1931 | 173 | 174 | 170 |
| MC1940 | 212 | — | 212 |
| MC2047 | 144 | 144 | 153 |
| MC2086 | 240 | — | 240 |
| MC2122 | 236 | — | 236 |
| MC2132 | 254 | 223 | 254 |
| MC2238 | 195 | 195 | 212 |
| MC2259 | 181 | — | 177 |
| MC2305 | 216 | — | — |
| NC004 | 148 | — | 170 |
| NC009 | 134 | 134 | 134 |
| PHI024 | 177 | — | 171 |
| PHI031 | 198 | 198 | 198 |
| PHI033 | 257 | 257 | 257 |
| PHI037 | 137 | — | 137 |
| PHI050 | 90 | 92 | 86 |
| PHI051 | 149 | 149 | 149 |
| PHI061 | 85 | 85 | 93 |
| PHI064 | 92 | — | 86 |
| PHI065 | 138 | 138 | 158 |
| PHI072 | 149 | 149 | 149 |
| PHI078 | 133 | 133 | 133 |
| PHI089 | 100 | 100 | 93 |
| PHI093 | 300 | 292 | 293 |
| PHI096 | 109 | — | 109 |
| PHI116 | 177 | — | 177 |
| PHI119 | 168 | 176 | 168 |
| PHI120 | 76 | — | 75 |

Primers used to detect SSRs are from Celera AgGen, Inc., 1756 Picasso Ave., Davis, CA 95616

Another aspect of this invention is a plant genetic complement characterized by a genetic isozyme typing profile. Isozymes are forms of proteins that are distinguishable, for example, on starch gel electrophoresis, usually by charge and/or molecular weight. The techniques and nomenclature for isozyme analysis are described in, for example, Stuber et al. (1988), which is incorporated by reference.

A standard set of loci can be used as a reference set. Comparative analysis of these loci is used to compare the purity of hybrid seeds, to assess the increased variability in hybrids compared to inbreds, and to determine the identity of seeds, plants, and plant parts. In this respect, an isozyme reference set can be used to develop genotypic "fingerprints."

Table 7 lists the identifying numbers of the alleles at isozyme loci types, and represents the exemplary genetic isozyme typing profile for LIZL5.

TABLE 7

Isozyme Profile of LIZL5 and Comparative Inbreds

| | ISOZYME ALLELE | | |
|---|---|---|---|
| LOCI | LIZL5 | 01IBH2 | MM402A |
| Acph1 | 2 | 2 | 4 |
| Adh1 | 4 | 4 | 4 |
| Cat3 | 9 | 9 | 9 |
| Got3 | 4 | 4 | 4 |
| Got2 | 4 | 4 | 4 |
| Got1 | 4 | 4 | 4 |
| Idh1 | 4 | 4 | 4 |
| Idh2 | 4 | 4 | 6 |
| Mdh1 | 6 | 6 | 6 |
| Mdh2 | 6 | 3 | 6 |
| Mdh3 | 16 | 16 | 16 |
| Mdh4 | 12 | 12 | 12 |
| Mdh5 | 12 | 12 | 12 |
| Pgm1 | 9 | 9 | 9 |
| Pgm2 | 4 | 4 | 4 |
| 6Pgd1 | 2 | 3.8 | 2 |
| 6Pgd2 | 5 | 5 | 5 |
| Phi1 | 4 | 4 | 4 |

The present invention also provides a hybrid genetic complement formed by the combination of a haploid genetic complement of the corn plant LIZL5 with a haploid genetic complement of a second corn plant. Means for combining a haploid genetic complement from the foregoing inbred with another haploid genetic complement can comprise any method for producing a hybrid plant from LIZL5. It is contemplated that such a hybrid genetic complement can be prepared using in vitro regeneration of a tissue culture of a hybrid plant of this invention.

A hybrid genetic complement contained in the seed of a hybrid derived from LIZL5 is a further aspect of this invention. An exemplary hybrid genetic complement is that of the hybrid 7026255.

Table 8 shows the identifying numbers of the alleles for the hybrid 7026255, which constitutes an exemplary SSR genetic marker profile for hybrids derived from the inbred of the present invention. Table 8 concerns 7026255, which has LIZL5 as one inbred parent.

TABLE 8

SSR Profile of 7026255

| LOCUS | Hybrid 7026255 |
|---|---|
| BNGL105 | 92.92 |
| BNGL118 | 110.110 |
| BNGL149 | 183.183 |
| BNGL426 | 119.119 |
| BNGL589 | 175.175 |
| BNGL615 | 194.231 |
| BNGL619 | 275.267 |
| DUP14 | 76.112 |
| DUP28 | 131.123 |
| MC1014 | 163.169 |
| MC1017 | 196.196 |
| MC1018 | 140.138 |
| MC1022 | 116.116 |
| MC1043 | 165.175 |
| MC1065 | 219.230 |
| MC1070 | 239.220 |
| MC1074 | 164.186 |
| MC1094 | 170.184 |
| MC1129 | 204.206 |
| MC1138 | 188.196 |
| MC1176 | 220.254 |
| MC1191 | 213.202 |
| MC1194 | 143.143 |
| MC1208 | 111.111 |
| MC1209 | 184.184 |
| MC1237 | 159.161 |
| MC1257 | 180.229 |
| MC1265 | 220.246 |
| MC1287 | 160.160 |
| MC1305 | 16.1600 |
| MC1325 | 171.179 |
| MC1329 | 95.93 |
| MC1371 | 95.124 |
| MC1449 | 95.160 |
| MC1456 | 176.187 |
| MC1484 | 124.117 |
| MC1520 | 299.275 |
| MC1523 | 199.199 |
| MC1538 | 213.237 |
| MC1605 | 110.128 |
| MC1662 | 151.132 |
| MC1782 | 228.228 |
| MC1784 | 254.250 |
| MC1831 | 182.186 |
| MC1890 | 163.136 |
| MC1904 | 191.183 |
| MC1931 | 17.1693 |
| MC1940 | 212.222 |
| MC2047 | 144.146 |
| MC2086 | 240.240 |
| MC2122 | 236.254 |
| MC2132 | 254.223 |
| MC2238 | 195.186 |
| MC2259 | 181.203 |
| MC2305 | 216.218 |
| NC004 | 148.156 |
| NC009 | 134.119 |
| PHI024 | 177.171 |
| PHI031 | 198.194 |
| PHI033 | 257.257 |
| PHI037 | 137.141 |
| PHI050 | 90.92 |
| PHI051 | 149.147 |
| PHI061 | 85.85 |
| PHI065 | 138.138 |
| PHI072 | 149.149 |
| PHI078 | 133.131 |
| PHI089 | 100.93 |
| PHI093 | 300.299 |
| PHI096 | 109.109 |
| PHI116 | 177.181 |
| PHI120 | 76.70 |

Primers used to detect SSRs are from Celera AgGen, Inc., 1756 Picasso Ave., Davis, CA 95616

The exemplary hybrid genetic complements of hybrid 7026255 may also be assessed by genetic isozyme typing profiles using a standard set of loci as a reference set, using, e.g., the same, or a different, set of loci to those described above. Table 9 lists the identifying numbers of the alleles at isozyme loci types and presents the exemplary genetic isozyme typing profile for the hybrid 7026255, which is an exemplary hybrid derived from the inbred of the present invention. Table 9 concerns 7026255, which has LIZL5 as one inbred parent.

TABLE 9

Isozyme Profile for Hybrid 7026255

| Loci | Isozyme Allele |
| --- | --- |
| Acph1 | 2/4 |
| Adh1 | 4 |
| Cat3 | 9 |
| Got3 | 4 |
| Got2 | 4 |
| Got1 | 4 |
| Idh1 | 4 |
| Idh2 | 4/6 |
| Mdh1 | 6 |
| Mdh2 | 6 |
| Mdh3 | 16 |
| Mdh4 | 12 |
| Mdh5 | 12 |
| Pgm1 | 9 |
| Pgm2 | 4 |
| 6-Pgd1 | 2/3.8 |
| 6-Pgd2 | 5 |
| Phi1 | 4 |

XI. Methods for Plant Transformation

Suitable methods for plant transformation for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, maize cells as well as those of virtually any other plant species may be stably transformed, and these cells developed into transgenic plants. In certain embodiments, acceleration methods are preferred and include, for example, microprojectile bombardment and the like.

A. Electroporation

Where one wishes to introduce DNA by means of electroporation, it is contemplated that the method of Krzyzek et al. (U.S. Pat. No. 5,384,253, incorporated herein by reference in its entirety) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. In particular, intact cells of maize may be transformed by electroporation (U.S. Pat. No. 5,384,253; Rhodes et al., 1995; D'Halluin et al., 1992).

One also may employ protoplasts for electroporation transformation of plants (Bates, 1994; Lazzeri, 1995). For example, protoplast transformation has been described for maize by Bhattacharjee et al., (1997).

B. Microprojectile Bombardment

A preferred method for delivering transforming DNA segments to plant cells in accordance with the invention is microprojectile bombardment (U.S. Pat. No. 5,489,520; U.S. Pat. No. 5,538,880; and U.S. Pat. No. 6,025,545; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

C. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into dicot plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of many dicots. However, recent advances in *Agrobacterium*-mediated transformation techniques have now made the technique applicable to many monocotyledonous plants, including maize. For example, *Agrobacterium*-mediated transformation techniques applicable to maize were described by Ishidia et al., (1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

D. Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988). Application of these systems to different plant strains depends upon the ability to regenerate that particular plant strain from protoplasts. Illustrative methods for the use of direct uptake transformation of maize were described by maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cell are punctured. This technique has been used successfully with, for example, the monocot cereals maize (PCT Application WO 95/06128, specifically incorporated herein by reference in its entirety; Thompson, 1995) and rice (Nagatani, 1997).

XII. Tissue Culture and Transformation of LIZL5

A. Transformation of LIZL5 by Microprojectile Bombardment

1. Initiation of Cultures and Preparation of Tissue for Microprojectile Bombardment.

Embryogenic callus was initiated from immature embryos derived from LIZL5. Donor plants were grown in the greenhouse. Plants grown in a field or growth chamber could also be used. Immature embryos were collected when the embryos were about 1.5–2.0 mm in length, usually 10–15 days following pollination, most commonly 12 days after pollination. Husks and silks were removed and ears sterilized by spraying or soaking with 80% ethanol and air drying in a laminar flow hood. Alternatively, ears were surface sterilized with 50% CLOROX containing 10% SDS for 20 minutes, followed by three rinses in sterile water. Alternative methods of sterilization of ears and excision of immature embryos were described by Armstrong (Armstrong, 1993). Immature embryos were cultured with the embryonic axis contacting medium 211V (N6 salts (Chu et al, 1975), 1 mg/L 2,4-D, 0.5 mg/L niacin, 1.0 mg/L thiamine, 0.91 g/L L-asparagine, 100 mg/L myo-inositol, 0.5 g/L MES, 100 mg/L casein hydrolysate, 1.6 g/L $MgCl_2.6H_2O$, 0.69 g/L L-proline, 100 µM $AgNO_3$ and 2 g/L Gelgro). Immature embryos and developing callus were subcultured to fresh medium 211V, preferably at about one week intervals for 3 weeks. Type I callus was removed from embryos as it developed and subcultured on 211 medium (N6 salts (Chu et al, 1975), 1 mg/L 2,4-D, 0.5 mg/L niacin, 1.0 mg/L thiamine, 0.91 g/L L-asparagine, 100 mg/L myo-inositol, 0.5 g/L MES, 100 mg/L casein hydrolysate, 1.6 g/L $MgCl_2.6H_2O$, 0.69 g/L L-proline, and 2 g/L Gelgro) preferably at two week intervals. During initiation and maintenance of type I callus, cells are subcultured at one to four week intervals, preferably at two to three week intervals. Methods for initiation and maintenance of type I callus may be successfully varied as known to those of skill in the art. For example, a variety of phytohormones may be used, such as, but not limited to 2,4-D, dicamba, pichloram, indole acetic acid, and naphthalene acetic acid. Furthermore, concentrations of phytohormones may be varied. For example, concentrations of 2,4-D from 0.5 to 20.0 mg/L may be successfully used to initiate and maintain type I callus. Preferably 0.5 mg/L to 5.0 mg/L 2,4-D is used and most preferably, 1.0 to 1.5 mg/L 2,4-D is used to initiate and maintain type I callus. In addition, other culture medium components may be varied in concentration or omitted form the culture medium, e.g., $AgNO_3$, L-proline and the such. Furthermore, salts such as MS (Murashige and Skoog, 1962) may be substituted for N6 salts. Established type I callus may be used as recipient cells for microprojectile bombardment or *Agrobacterium* mediated transformation. For example, in a study designated EE26, for which results are described below, about 150 pieces of type I callus were bombarded with the plasmid pMON30460 (FIG. 1).

Preferably, for microprojectile bombardment, LIZL5 immature embryos were cultured for 3–7 days after excision on 211V medium. In an experiment designated EE61, for which results are described below, 150 LIZL5 immature embryos were bombarded 6 days after isolation. Approximately 4 hours prior to bombardment, about 25 precultured immature embryos were transferred to each petri dish containing 211V medium containing 12% sucrose, designated medium 211SV. Embryos were positioned with the scutellar end towards the center of the plate side by side on the circumference of a "nickel." The other end of the embryo was pressed into the media at a 20 degree angle, thereby optimizing the surface area of the responding scutellar surface for microprojectile bombardment. Tissue was kept in the dark prior to bombardment. Typically a bombardment experiment comprised 100–200, usually 150, immature embryos or pieces of type I callus.

2. Pre-Selected DNA

Pre-selected DNA may comprise any nucleic acid desired to be introduced into a cell, for example, an expression cassette comprising a selectable marker gene, and usually, at least one other expression cassette comprising a gene of interest, i.e., a gene which confers a desirable phenotype on a transformed cell or plant. A gene of interest often does not confer a phenotype on the plant that is selectable, e.g., alterations in nutritional composition, insect or disease resistance. The selectable marker and genes of interest may be present on a single plasmid vector or may be present on separate plasmid vectors. Most preferably the expression cassette comprising a selectable marker gene comprises a Cauliflower Mosaic Virus 35S promoter operable linked to a gene encoding neomycin phosphotransferase (nptII) and a 3' region derived from the *Agrobacterium tumefaciens* nopaline synthase (nos) gene. Expressions of the nptII expression cassette confers resistance to the antibiotics kanamycin, neomycin, G418 and paromomycin. An exemplary plasmid vector comprising the nptII expression cassette is pMON30460 (FIG. 1). One of skill in the art will recognize that many other selectable marker genes that may be useful for selection of transformed plant cells and plants.

Selectable marker genes may include, for example, genes encoding phosphinothricin acetyltransferase, e.g., bar or pat, glyphosate resistant EPSPS encoding genes, or genes encoding dehalogenase enzymes that confer resistance to halogenated aliphatic compounds such as 2,2-dichloroproprionic acid (dalapon). Further selectable markers genes are disclosed in, for example, U.S. Pat. No. 5,990,390. It is contemplated that many genes of interest could be introduced into LIZL5. Genes of interest may encode proteins conferring traits including, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress, or oxidative stress; increased yields; food content and makeup; physical appearance; male sterility; dry-down; standability; prolificacy; starch properties; oil quantity and quality, and the like.

3. DNA/Gold Precipitation Procedure

Sixty milligrams of 0.6 micron gold (BioRad (Hercules, Calif.) or ASI (Richmond, Calif.)) was suspended in 1.0 ml absolute ethanol. The solution of gold particles was sonicated for 1 minute, or alternatively, vortexed for 1 minute followed by sonication for 1 minute, or vortexed only. The gold solution was stored at $-20°$ C. Prior to use, the gold stock was vortexed for 1 minute, or vortexed for 30 seconds followed by sonication for 30 seconds. 30 µl of gold solution was removed from the top $\frac{1}{3}$ of the resuspended stock and transferred to a sterile tube. Ethanol was removed by centrifugation and the gold particle pellet was washed with sterile water. The washed gold particles were pelleted by centrifugation and resuspended in a solution containing 0.5 ng to 25 µg, and preferably 25–100 ng, of pre-selected DNA. Transformants were recovered following bombardment with gold particles precipitated with various amounts of pre-selected DNA. The pre-selected DNA may comprise one or more plasmid vectors. For example, in study EE26, 25 ng of plasmid pMON30460 (FIG. 1) and 35 ng of plasmid pDPG915, comprising a non-selectable gene of interest, were co-precipitated on gold particles. In study EE61, 100 ng of plasmid pMON30460 (FIG. 1) and 100 ng of plasmid pDPG915 were co-precipitated onto gold particles. Sterile water was added to bring the volume to 245 µl followed by addition of 250 µl 2.5M $CaCl_2$ and 50 µl 0.1M spermidine. The gold/DNA mix was vortexed for 10 minutes at $4°$ C. The DNA/gold precipitate was collected by centrifugation and washed in absolute ethanol. The washed DNA/gold pellet was resuspended in 36–38 ml absolute ethanol.

The DNA/gold precipitate was vortexed or sonicated for up to 20 seconds prior to application of particles to a macrocarrier for use in the Bio-Rad Biolistics PDS-1000/He device. Particles were usually allowed to settle for 1–2 minutes and then 5.0–8.0 µl of the DNA/gold preparation was applied to a macrocarrier (Bio-Rad, Hercules, Calif.; or ASI, Richmond, Calif.) and allowed to dry.

Tissue was bombarded according to the manufacturer's instructions (Bio-Rad, Hercules, Calif.) for the Biolistics PDS-1000/He particle delivery system using a 1100 psi rupture disk.

4. Selection of Transformants

Twenty-four hours after bombardment, immature embryos were transferred to medium 211 with 25 mg/L paromomycin and 100 µM $AgNO_3$ (medium 211HV). Tissue was incubated in the dark at $27°$ C. Tissue was transferred at 2–3 week intervals to fresh medium 211 containing 50 mg/L paromomycin (medium 211G) and subsequently transferred at 2–4 week intervals for up to 20 weeks. At each transfer, healthy yellow tissue was subcultured. Preferably tissue was transferred to fresh culture medium every 3 weeks and transformants identified following 9–12 weeks culture on selection medium. Alternatively, transformations were selected by transferring cultures on 211L every 2 weeks for up to 6 weeks, or every week for up to 3 weeks. In experiment. In experiment EE61, tissue was initially cultured on 211HV medium followed by subculture every 3 to 3½ weeks onto medium 211G (25 mg/L paromomycin) or 211H (50 mg/L paromomycin), and four transformants from which fertile transgenic plants were produced were recovered. In this study transformants were identified on medium 211H about 13 weeks after initiation of selection.

Transformants were recovered following bombardment of LIZL5 type I callus in study EE26. Type I callus was bombardment with the plasmid vector pMON30460 (FIG. 1), initially cultured on medium 211G (50 mg/L paromomycin), followed by subculture every 2 weeks for 7 weeks on medium 211T (100 mg/L paromomycin). Fertile transgenic plants were produced from 3 transformants recovered from study EE26.

Concentrations of paromomycin may be varied, ranging from 10 mg/L to 500 mg/L, preferably 25 mg/L to 250 mg/L and most preferable from 25 mg/L to 100 mg/L. Using these methods, transformants were recovered from established type I callus or immature embryos cultured less than 7 days.

5. Plant Regeneration

Transformants were transferred to medium 217 (N6 salts; 5 mg/L thiamine; 2.5 mg/L niacin; 17.6 mg/L 6-benzylaminopurine (BAP); 4.55 g/L L-asparagine monohydrate; 500 mg/L myo-inositol; 2.5 g/L MES; 8 g/L $MgCL_2.6H_2O$; 500 mg/L casein hydrolysate; 3.45 g L-proline; 100 g/L sucrose; 2 g/L Gelgro; adjusted to pH 5.8) for 5–12 days at $25°$ C. in the dark. Tissue was transferred to medium 127 (MS salts; 650 µg/L niacin; 125 µg/L pyridoxine.HCl; 125 mg/L thiamine.HCl; 125 µg/L calcium pantothenate; 750 mg/L L-asparagine; 500 mg/L myo-inositol; 5.5 g/L Phytagar; 1 g/L L-glucose; 2 g/L L-maltose) containing 100 mg/L paromomycin (designated 127T). Plantlets were transferred to soil 3–6 weeks after transfer to medium 127T. $R_0$ plants were grown in the greenhouse and crossed as a male or female parent to sibling LIZL5 plants (or other inbreds) or self-pollinated. Seed produced by transgenic LIZL5 was used for breeding and assayed for transgene expression in seed itself or in progeny plants of any generation. One of skill in the art will recognize that alternative methods are available for regenerating fertile plants from embryogenic callus.

B. Transformation of LIZL5 Using *Agrobacterium tumefaciens*

Figure 2:
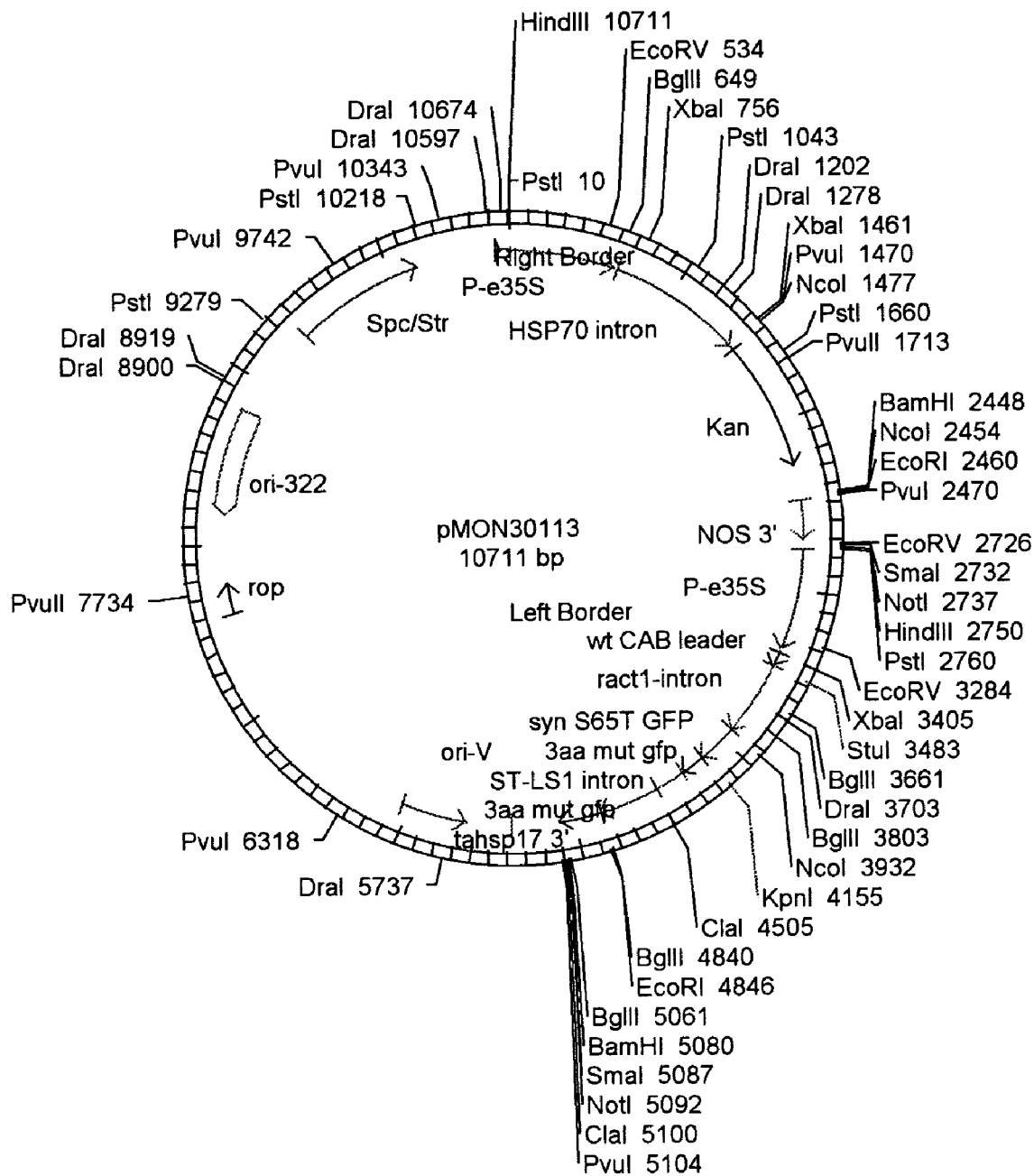
FIG. 2 is a depiction of plasmid vector pMON30113. The plasmid comprises an expression cassette containing a Cauliflower Mosaic Virus 35S promoter operably linked to an hsp70 intron, a neomycin phosphotransferase II coding sequence, and termination and polyadenylation signal sequences derived from the nopaline synthase gene. PMON30113 further contains an expression cassette comprising a Cauliflower Mosaic Virus 35S promoter operably linked to a rice actin 1 intron 1 sequence, a green fluorescent protein coding sequence, and termination and polyadenylation signal sequences derived from the hsp17 gene.

Methods of *Agrobacterium* mediated transformation of maize and other monocots are known (Hiei, Y. et al., 1997; U.S. Pat. No. 5,591,616; U.S. Pat. No. 5,981,840; published EP patent application EP 672752). It is believed by the inventors that various species of *Agrobacterium* may be used in the practice of the present invention, including *Agrobacterium tumefaciens* and *Agrobacterium rhizogenes*. Although various strains of *Agrobacterium* may be used (see references above), *Agrobacterium tumefaciens* strain ABI was used preferably by the present inventors. The ABI strain of *Agrobacterium* is derived from strain A208, a C58 nopaline type strain (ATCC deposit number 33970), from which the Ti plasmid was eliminated by culture at $37°$ C., and contains the modified Ti plasmid pMP90RK (Koncz, C. and Schell, J., 1986). The ABI strain is useful in a binary vector system (An, 1988) to transform LIZL5. Alternative cointegrating Ti plasmid vectors have been described (Rogers, S. G. et al., 1988) and could be used to transform LIZL5. A binary vector comprising one or more genes of interest was introduced into a disarmed *Agrobacterium* strain using electroporation (Wen-jun, S. and Forde, B. G., 1989) or triparental mating (Ditta, G., et al., 1980). A binary vector may contain a selectable marker gene, a screenable marker gene and/or one or more genes that confer a desirable phenotypic trait on the transformed plant. An exemplary binary vector, pMON30113, used by the inventors is shown in FIG. 2. Other binary vectors may be used and are known to those of skill in the art.

Prior to co-culture of LIZL5 cells, *Agrobacterium* cells were grown at 28° C. in LB liquid medium (10 g/L Bactotryptone (Difco Laboratories, Inc., Livonia, Mich.), 5 g/L Bacto-yeast extract (Difco Laboratories, Livonia, Mich.), 10 g/L NaCl, pH 7.0) comprising appropriate antibiotics to select for maintenance of the modified Ti plasmid and binary vector. For example, ABI/pMON30113, was grown in LB medium containing 50 ug/ml kanamycin to select for maintenance of the pMP90RK modified Ti plasmid and 100 ug/ml spectinomycin to select for maintenance of the binary vector pMON30113. It will be apparent to one of skill in the art to use appropriate selection agents to maintain plasmids in the host *Agrobacterium* strain. Prior to inoculation of LIZL5 cells, *Agrobacterium* cells were grown overnight at room temperature in AB medium (Chilton, M. et al., 1974) comprising appropriate antibiotics for plasmid maintenance and 200 uM acetosyringone. Immediately prior to inoculation of maize cells, *Agrobacterium* was pelleted by centrifugation, washed in ½ MSVI medium (2.2 g/L GIBCO MS salts, 2 mg/L glycine, 0.5 g/L niacin, 0.5 g/L L-pyridoxine-HCl, 0.1 mg/L thiamine, 115 g/L L-proline, 10 g/L D-glucose, and 10 g/L sucrose, pH 5.4) containing 200 uM acetosyringone, and resuspended at 0.001 to $1.0 \times 10^{10}$ cells/ml in ½ MSPL medium (2.2 g/L GIBCO MS salts, 2 mg/L glycine, 0.5 g/L niacin, 0.5 g/L L-pyridoxine-HCl, 0.1 mg/L thiamine, 115 g/L L-proline, 26 g/L D-glucose, 68.5 g/L sucrose, pH 5.4) containing 200 uM acetosyringone.

LIZL5 immature embryos were isolated as described previously and placed in ½ MSPL medium immediately following excision and held for 1–2 hours prior to inoculation with *Agrobacterium*. Medium ½ MSPL was removed and immature embryos incubated in ½ MSPL medium containing *Agrobacterium*, prepared as described above, for 5 minutes. Alternatively, immature embryos could be cultured for more than 7 days. For example, embryogenic callus could be initiated as described above and co-cultured with *Agrobacterium*. Preferably, LIZL5 immature embryos were excised, immersed in an *Agrobacterium* suspension in ½ MSPL medium prepared as described above and incubated at room temperature with *Agrobacterium* for 5–20 minutes.

Following inoculation, embryos were transferred to one-half strength MS medium (Murashige, T. and Skoog, F, 1962) containing 3.0 mg/L 2,4-dichlorophenyoxyacetic acid (2,4-D), 1% D-glucose, 2% sucrose, 0.115 g/L L-proline, 0.5 mg/L thiamine-HCl, 200 uM acetosyringone, and 20 uM silver nitrate or silver thiosulfate. Immature embryos were co-cultured with *Agrobacterium* for 1 to 3 days at 23° C. in the dark.

Co-cultured embryos were transferred to Duncan's medium D (Duncan, D. R. et al., 1985), or MS medium containing 1.5 mg/L 2,4-D, 500 mg/L carbenicillin, 3% sucrose, 1.38 g/L L-proline and 20 uM silver nitrate or silver thiosulfate and cultured for 0 to 8 days in the dark at 27° C. without selection. All culture media used for selection of transformants and regeneration of plants contained 500 mg/L carbenicillin. In the absence of a delay of selection (0 day culture), selection was initiated on 25 mg/L paromomycin. Selection medium comprised medium 211 (described above) or a variant of medium 211 in which N6 salts were replaced by MS salts. After two weeks, embryogenic callus was transferred to culture medium containing 100 mg/L paromomycin and subcultured at about two week intevals. When selection was delayed following co-culture, embryos were initially cultured on medium containing 50 mg/L paromomycin followed by subsequent culture of embryogenic callus on medium containing 100–200 mg/L paromomycin. It is believed that initial culture on 25 to 50 mg/L paromocyin for about two weeks, followed by culture on 50–200 mg/L paromoycin will result in recovery of transformed callus. Transformants were recovered 6 to 8 weeks after initiation of selection.

Plants were regenerated from transformed embryogenic callus as described above for transformants recovered following microprojectile bombardment. Seed was recovered from two transformants into which plasmid pMON30113 was introduced using *Agrobacterium tumefaciens*.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

An et al., Plant Molecular Biology Manual A3: 1–19, 1988
Anderson, W. P., Weed Science Principles, West Publishing Company, 1983.
Armstrong and Green, "Establishment and maintenance of friable, embryogenic maize callus and the involvement of L-proline," *Planta*, 164:207–214, 1985.
Armstrong, C. L., "Regeneration of Plants from Somatic Cell Cultures: Applications for in vitro Genetic Manipulation" in The Maize Handbook, Freeling, M. and Walbot, V., eds., 1993.
Bates, "Genetic transformation of plants by protoplast electroporation," *Mol Biotechnol.*, 2(2):135–145, 1994.
Bhattacharjee; An; Gupta, *J. Plant Bioch. and Biotech.* 6, (2):69–73. 1997.
Callis et al., *Genes Dev.*, 1:1183–1200, 1987.
Chilton, M. et al., Proc. Natl. Acad. Sci. USA 71: 3672–3676, 1974.
Chu et al., Scientia Sinica 18:659–668. 1975.

Conger, Novak, Afza, Erdelsky, "Somatic Embryogenesis from Cultured Leaf Segments of Zea Mays," *Plant Cell Reports*, 6:345–347, 1987.

D'Halluin et al., "Transgenic maize plants by tissue electroporation," *Plant Cell*, 4(12):1495–1505, 1992.

Ditta, G., et al. Proc. Natl. Acad. Sci. USA 77: 7374–7351, 1980.

Duncan et al., "The Production of Callus Capable of Plant Regeneration from Immature Embryos of Numerous *Zea Mays* Genotypes," *Planta*, 165:322–332, 1985.

Fehr, "Theory and Technique," *In: Principles of Cultivar Development*, 1:360–376, 1987.

Fromm et al., "Stable transformation of maize after gene transfer by electroporation," *Nature*, 319:791–793, 1986

Gaillard et al., "Optimization of Maize Microspore Isolation and Culture Condition for Reliable Plant Regeneration," *Plant Cell Reports*, 10(2):55, 1991.

Gordon-Kamm et al., "Transformation of Maize Cells and Regeneration of Fertile Transgenic Plants," *The Plant Cell*, 2:603–618, 1990.

Green and Rhodes, "Plant Regeneration in Tissue Cultures of Maize: Callus Formation from Stem Protoplasts of Corn (*Zea Mays* L.)," *In: Maize for Biological Research*, 367–372, 1982.

Hiei, Y. et al. Plant Mol. Biol. 35: 205–218, 1997

Jensen, "Chromosome Doubling Techniques in Haploids," *Haploids and Higher Plants—Advances and Potentials, Proceedings of the First International Symposium*, 1974.

Kaeppler et al., "Silicon carbide fiber-mediated stable transformation of plant cells," *Theor. Appl. Genet.*, 84(5–6): 560–566, 1992.

Kaeppler et al., *Plant Cell Reports* 9: 415–418, 1990.

Klee et al., *Bio-Technology*, 3(7):637–642, 1985.

Knittel et al., *Plant Cell Reports*, 14(2–3):81–86, 1994.

Koncz, C. and Schell, J., Molec. Gen. Genet. 204: 383–396, 1986.

Lazzeri, "Stable transformation of barley via direct DNA uptake. Electroporation- and PEG-mediated protoplast transformation," *Methods Mol. Biol.*, 49:95–106, 1995.

Lee et al., *Korean J Genet.*, 11(2):65–72, 1989.

Lorz et al., *Mol Gen Genet*, 199:178–182, 1985.

Marcotte et al., *Nature*, 335:454, 1988.

Murashige, T. and Skoog, F. Physiol. Plant. 15: 473–497, 1962.

Nagatani et al., "DNA delivery into rice cells and transformation using silicon carbide whiskers," *Biotech. Tech.*, 11(7):471–473, 1997.

Nienhuis et al., "Restriction Fragment Length Polymorphism Analysis of Loci Associated with Insect Resistance in Tomato," *Crop Science*, 27(4):797–803, 1987.

Omirulleh et al., "Activity of a chimeric promoter with the doubled CaMV 35S enhancer element in protoplast-derived cells and transgenic plants in maize." *Plant Mol. Biol.*, 21:415–28, 1993.

Omirulleh et al., "Activity of a chimeric promoter with the doubled CaMV 35S enhancer element in protoplast-derived cells and transgenic plants in maize," *Plant Mol. Biol.*, 21(3):415–428, 1993.

Pace et al., "Anther Culture of Maize and the Visualization of Embryogenic Microspores by Fluorescent Microscopy," *Theoretical and Applied Genetics*, 73:863–869, 1987.

Poehlman et al., "Breeding Field Crops," 4th Ed., Iowa State University Press, Ames, Iowa, pp 132–155 and 321–344, 1995.

Potrykus et al., *Mol. Gen. Genet.*, 199:183–188, 1985.

Rao et al., "Somatic Embryogenesis in Glume Callus Cultures," *Maize Genetics Cooperation Newsletter*, 60, 1986.

Rhodes et al., "Transformation of maize by electroporation of embryos," *Methods Mol. Biol.*, 55:121–131, 1995.

Rogers et al., *Methods Enzymol.*, 153:253–277, 1987.

Rogers, S. G. et al., Plant Molecular Biology Manual A2: 1–12, 1988.

Songstad et al., "Effect of 1-Aminocyclopropate-1-Carboxylic Acid, Silver Nitrate, and Norbornadiene on Plant Regeneration from Maize Callus Cultures," *Plant Cell Reports*, 7:262–265, 1988.

Sprague and Dudley (eds.), "Corn and Corn Improvement," 3rd Ed., Crop Science of America, Inc., and Soil Science of America, Inc., Madison Wis. pp 881–883 and pp 901–918, 1988.

Stuber et al., "Techniques and scoring procedures for starch gel electrophoresis of enzymes of maize C. *Zea mays*, L.," *Tech. Bull.*, 286, 1988.

Thompson et al., "Maize transformation utilizing silicon carbide whiskers: A review," *Euphytica*, 85(1–3):75–80, 1995.

Uchimiya et al., *Mol. Gen. Genet.*, 204:204, 1986.

Vasil et al., *Plant Physiol.*, 91:1575–1579, 1989.

Wan et al., "Efficient Production of Doubled Haploid Plants Through Colchicine Treatment of Anther-Derived Maize Callus," *Theoretical and Applied Genetics*, 77:889–892, 1989.

Wang et al., "Large-Scale Identification, Mapping, and Genotyping of Single-Nucleotide Polymorphisms in the Human Genome," *Science*, 280:1077–1082, 1998.

Wen-jun, S. and Forde, B. G. Nucl. Acid. Res. 17: 8385, 1989.

Williams et al., "Oligonucleotide Primers of Arbitrary Sequence Amplify DNA Polymorphisms which Are Useful as Genetic Markers," *Nucleic Acids Res.*, 18:6531–6535, 1990.

What is claimed is:

1. Inbred corn seed of the corn plant LIZL5, a sample of said seed having been deposited under ATCC Accession No. PTA-2192.

2. An essentially homogeneous population of corn seed consisting essentially of the inbred corn seed of claim 1.

3. A population of corn seeds consisting essentially of the inbred corn seed of claim 1, wherein the population is essentially free from hybrid seed.

4. An inbred corn plant produced by growing the seed of the inbred corn plant LIZL5, a sample of said seed having been deposited under ATCC Accession No. PTA-2192.

5. Pollen of the plant of claim 4.

6. An ovule of the plant of claim 4.

7. An essentially homogeneous population of corn plants produced by growing a population of corn seed consisting essentially of the seed of the inbred corn plant LIZL5, a sample of said seed of the inbred corn plant LIZL5 having been deposited under ATCC Accession No. PTA-2192.

8. A corn plant expressing all the physiological and morphological characteristics of the inbred corn plant LIZL5, a sample of the seed of said inbred corn plant LIZL5 having been deposited under ATCC Accession No. PTA-2192.

9. The corn plant of claim 8, further comprising a cytoplasmic or nuclear gene conferring male sterility.

10. A tissue culture of regenerable cells of inbred corn plant LIZL5, wherein the tissue regenerates plants expressing all the physiological and morphological characteristics of the inbred corn plant LIZL5, a sample of the seed of said inbred corn plant LIZL5 having been deposited under ATCC Accession No. PTA-2192.

11. The tissue culture of claim 10, wherein the regenerable cells comprise cells derived from embryos, immature embryos, meristematic cells, immature tassels, microspores, pollen, leaves, anthers, roots, root tips, silk, flowers, kernels, ears, cobs, husks, or stalks.

12. The tissue culture of claim 11, wherein the regenerable cells are in the form of protoplasts or callus.

13. A corn plant regenerated from the tissue culture of claim 10, wherein said corn plant is expresses all of the physiological and morphological characteristics of the inbred corn plant designated LIZL5, a sample of the seed of said inbred corn plant designated LIZL5 having been deposited under ATCC Accession No. PTA-2192.

14. An inbred corn plant cell of the corn plant of claim 8, said cell comprising:
 (a) an SSR genetic marker profile in accordance with the profile shown in Table 6; or
 (b) a genetic isozyme typing profile in accordance with the profile shown in Table 7.

15. A corn seed comprising the inbred corn plant cell of claim 14.

16. A tissue culture comprising the inbred corn plant cell of claim 14.

17. The inbred corn plant of claim 8, comprising:
 (a) an SSR genetic marker profile in accordance with the profile shown in Table 6; or
 (b) a genetic isozyme typing profile in accordance with the profile shown in Table 7.

18. A process of producing corn seed, comprising crossing a first parent corn plant with a second parent corn plant, wherein said first or second corn plant is the inbred corn plant LIZL5, a sample of the seed of said inbred corn plant LIZL5 having been deposited under ATCC Accession No. PTA-2192, wherein seed is allowed to form.

19. The process of claim 18, further defined as a process of producing hybrid corn seed, comprising crossing a first inbred corn plant with a second, distinct inbred corn plant, wherein said first inbred corn plant is the inbred corn plant LIZL5, a sample of the seed of said inbred corn plant LIZL5 having been deposited under ATCC Accession No. PTA-2192.

20. The process of claim 19, wherein crossing comprises the steps of:
 (a) planting in pollinating proximity seeds of said first and second inbred corn plants;
 (b) cultivating the seeds of said first and second inbred corn plants into plants that bear flowers;
 (c) emasculating the male flowers of said first or second inbred corn plant to produce an emasculated corn plant;
 (d) allowing cross-pollination to occur between said first and second inbred corn plants; and
 (e) harvesting seeds produced on said emasculated corn plant.

21. The process of claim 19, further comprising growing said hybrid seed to produce an F1 hybrid corn plant.

22. F1 hybrid corn seed produced by the process of claim 19.

23. A F1 hybrid corn plant produced by the process of claim 21.

24. The corn plant of claim 4, further comprising a single locus conversion.

25. The corn plant of claim 24, wherein the single locus was conferred by a transgene.

26. The corn plant of claim 24, wherein the locus is selected from the group consisting of a dominant allele and a recessive allele.

27. The corn plant of claim 24, wherein the locus confers a trait selected from the group consisting of herbicide resistance, insect resistance, resistance to bacterial, fungal, nematode or viral disease, waxy starch, and male sterility.

28. A method of preparing a transgenic maize cell comprising:
 a) providing cells of inbred corn plant LIZL5, a sample of the seed of the inbred LIZL5 having been deposited under ATCC Accession No. PTA-2192;
 b) contacting said cells with a pre-selected DNA; and
 c) identifying at least a first transgenic cell of inbred corn plant LIZL5 which has been transformed with said pre-selected DNA.

29. The method of claim 28, further comprising the step of:
 d) regenerating a fertile transgenic plant from said transgenic cell.

30. The method of claim 28, wherein said contacting comprises a method selected from the group consisting of microprojectile bombardment, PEG mediated transformation of protoplasts, electroporation, silicon carbide fiber mediated transformation, or *Agrobacterium*-mediated transformation.

31. The method of claim 30, wherein said contacting comprises use of microprojectile bombardment.

32. The method of claim 30, wherein said contacting comprises use of PEG mediated transformation of protoplasts.

33. The method of claim 30, wherein said contacting comprises use of electroporation.

34. The method of claim 30, wherein said contacting comprises use of silicon carbide fiber mediated transformation.

35. The method of claim 30, wherein said contacting comprises use of *Agrobacterium*-mediated transformation.

36. A fertile transgenic maize plant produced by the process of claim 29.

37. A seed of the fertile transgenic maize plant of claim 36, produced by crossing said fertile transgenic maize plant with another maize plant, wherein said seed comprises said pre-selected DNA.

38. A plant grown from the seed of claim 37, said plant comprising said pre-selected DNA.

* * * * *